US 8,058,477 B2

United States Patent
Hartwig et al.

(10) Patent No.: US 8,058,477 B2
(45) Date of Patent: Nov. 15, 2011

(54) PROCESS FOR THE SYNTHESIS OF ARYLAMINES FROM THE REACTION OF AN AROMATIC COMPOUND WITH AMMONIA OR A METAL AMIDE

(75) Inventors: John F. Hartwig, Champaign, IL (US); Qilong Shen, Champaign, IL (US)

(73) Assignee: Yale University, New Haven, CT (US)

( * ) Notice: Subject to any disclaimer, the term of this patent is extended or adjusted under 35 U.S.C. 154(b) by 580 days.

(21) Appl. No.: 12/282,492

(22) PCT Filed: Mar. 20, 2007

(86) PCT No.: PCT/US2007/007290
§ 371 (c)(1),
(2), (4) Date: Jan. 16, 2009

(87) PCT Pub. No.: WO2007/109365
PCT Pub. Date: Sep. 27, 2007

(65) Prior Publication Data
US 2009/0234126 A1 Sep. 17, 2009

Related U.S. Application Data

(60) Provisional application No. 60/784,729, filed on Mar. 21, 2006.

(51) Int. Cl.
C07C 209/10 (2006.01)
C07F 15/02 (2006.01)
C07D 217/22 (2006.01)
C07D 209/86 (2006.01)
B01J 31/18 (2006.01)

(52) U.S. Cl. .......... 564/407; 556/14; 546/143; 548/447; 502/152

(58) Field of Classification Search .................. 564/407; 556/14; 568/12, 17
See application file for complete search history.

(56) References Cited

U.S. PATENT DOCUMENTS

| 5,371,256 | A | * | 12/1994 | Togni et al. ...................... 556/14 |
| 5,463,097 | A | * | 10/1995 | Togni et al. ...................... 556/14 |
| 5,466,844 | A |   | 11/1995 | Spindler et al. |
| 5,563,308 | A |   | 10/1996 | Spindler et al. |
| 5,563,309 | A | * | 10/1996 | Togni et al. ................... 585/277 |
| 5,565,594 | A |   | 10/1996 | Spindler et al. |
| 5,576,460 | A |   | 11/1996 | Buchwald et al. |
| 5,583,241 | A | * | 12/1996 | Spindler ........................ 556/11 |
| 5,977,361 | A |   | 11/1999 | Hartwig et al. |
| 6,235,938 | B1 |  | 5/2001  | Hartwig et al. |
| RE37,344  | E | * | 8/2001  | Togni et al. ...................... 556/14 |
| 6,867,310 | B1 |  | 3/2005  | Buchwald et al. |

OTHER PUBLICATIONS

Hamann, et al., "Sterically Hindered Chelating Alkyl Phosphines Provide Large Rate Accelerations in Palladium-Catalyzed Amination of Aryl Iodides, Bromides, and Chlorides, and the First Amination of Aryl Tosylates," *J. Am. Chem. Soc.*, 1998, 120:7369-7370.
Lang, et al., "Amination of aryl halides using copper catalysis," *Tetrahedron Letters*, 2001, 42:3251-3254.
Lee, et al., "Palladium-Catalyzed Synthesis of Arylamines from Aryl Halides and Lithium Bis(trimethylsilyl)amide as an Ammonia Equivalent," *Org. Lett.*, 2001, 3(17):2729-2732.
Blaser et al., 2002, Topics in Catalysis 19(1):3-16.
Hayashi et al., 1980, Bull. Chem Soc. Jpn. 53(4):1138-51.
Huang et al., 2001, Org. Lett., 3:3417-19.
Jaime-Figueroa et al., 1998, Tetrahedron Lett. 29:1313-16.
Muci & Buchwald, 2002, Top. Curr. Chem. 219:131-209.
Shen et al., 2006, J. Am Chem Soc. 128:10028-29.
Wolfe et al., 1997, Tetrahedron Lett. 38:6368.

* cited by examiner

*Primary Examiner* — Brian J Davis
(74) *Attorney, Agent, or Firm* — Riverside Law LLP

(57) ABSTRACT

A catalytic process for the synthesis of aromatic primary amines, reagent compositions for effecting the process, and transition metal complexes useful in the process, are provided.

79 Claims, No Drawings

PROCESS FOR THE SYNTHESIS OF ARYLAMINES FROM THE REACTION OF AN AROMATIC COMPOUND WITH AMMONIA OR A METAL AMIDE

CROSS-REFERENCE TO RELATED APPLICATIONS

This application is the U.S. national phase application filed under 35 U.S.C. §371 claiming benefit to International Patent Application No. PCT/US2007/007290, filed on Mar. 20, 2007 and U.S. Provisional Patent Application No. 60/784,729, filed on Mar. 21, 2006, which is entitled to priority under 35 U.S.C. §119(a) each of which application is hereby incorporated herein by reference in its entirety.

FIELD OF THE INVENTION

This application relates to catalytic processes useful for the synthesis of aromatic primary amine compounds and novel complexes and compositions useful in such processes.

BACKGROUND

The aromatic amine moiety is a structural component in a variety of many useful organic compounds. Such compounds are useful in their own right, or as intermediates in the preparation of, for example, dyes, herbicides, insecticides, and pharmaceuticals. Aromatic primary amines are of particular interest and may be converted though derivatization to a wide variety of derivatives, for example via alkylation (to form secondary or tertiary amines), acylation (to form amides) or sulfonylation (to form sulfonamides).

New methods of synthesizing aromatic primary amines are needed. Many of the classical methods of preparing such compounds suffer from problems such as requiring harsh reaction conditions and are therefore lacking compatibility with other functional groups or selectivity, or being of limited scope.

A well-known procedure for the synthesis of aromatic primary amines involves nitration of an aromatic ring with an electrophilic nitrating agent, followed by reduction of the resulting aromatic nitro compound. The usefulness of the procedure may be limited by the lack of selectivity or inappropriate selectivity of the nitrating agent (typically nitric acid). Selectivity requires the reagent to attack one C—H bond selectively in the presence of other C—H bonds in the compound and other reactive functionalities in the substrate. For example, in substrates containing an activating group—a group that donates electrons to the aromatic ring—a mixture of nitrated products may be obtained wherein the nitro group is introduced ortho and/or para to the activating group. Further, activated substrates (electron rich aromatic groups) may be over-nitrated to give di- or tri-nitro derivatives. The nitrating agents are powerful oxidants, and therefore not compatible with all substrates. In addition, in order to effect conversion to the primary amine, selective reduction of the nitro group must be achieved.

Other methods of synthesizing aromatic amines involve substitution of existing functional groups. For example, nucleophilic substitution reactions of electron-deficient aromatic compound is efficient for certain substrates. See Hattori, et al., *Synthesis*, 1994, 199; and Bunnett, *Acc. Chem. Res.*, 1978, 11, 413. The usefulness of such reactions is generally limited to substrates that are activated to substitution via an $S_NAr$ mechanism, where an electron withdrawing group stabilizes the intermediate resulting from nucleophile addition to the position of the aromatic ring bearing a leaving group. A suitable electron withdrawing group disposed in a 1,2- or 1,4-position relative to the leaving group activates substrate to nucleophilic displacement by the $S_NAr$ mechanism by stabilizing the transition state to the intermediate in which the nucleophile is added to the aromatic ring. In suitable substrates, displacement can be achieved using an amine or ammonia as the nucleophile.

In nucleophilic substitution substrates that lack a suitable activating (i.e. electron-withdrawing) group, displacement of a leaving group can sometimes be achieved with powerfully basic anionic metal amides. However, rather than occurring via the $S_NAr$ addition-elimination mechanism, such displacements may occur via an elimination-addition mechanism proceeding via base-induced elimination of H—X (wherein X is the leaving group) to form an "aryne" intermediate, followed by addition of the amide to the C≡C bond of the aryne. Since the amide addition to the aryne may occur at either of the carbon atoms of the C≡C bond of the aryne, the amino group may be introduced either at the carbon at which the leaving group was located, or at an adjacent position (the latter being referred to as "cine substitution"). Thus, even if a substrate is compatible with the powerfully basic conditions for displacement with a metal amide, the substitution reaction may result in a mixture of products.

A very useful variation on the nucleophilic aromatic substitution reaction has been the use of organometallic catalysts in catalyzed cross-coupling reactions of substituted aromatic compounds with amino compounds. Such reactions typically involve an aromatic substrate having a halide or sulfonate leaving group reacted with an organic amine in the presence of an organometallic catalyst. The organometallic catalyst is typically a palladium catalyst comprising a phosphine ligand (usually a chelating phosphine ligand such as 2,2'-bis(diphenylphosphino)-1,1'-binaphthyl, or a sterically hindered monophosphine such as biphenyl-2-yldi-t-butylphosphine). The reaction is typically performed in the presence of a base such as sodium t-butoxide. Such reactions achieve an equivalent result to the nucleophilic displacement of the leaving group of the aromatic substrate with the amino compound. For references, see, e.g., J. Louie and J. F. Hartwig, *Tetrahedron Lett.*, 1995, 36, 3609; A. S. Guram, et al., *Angew. Chem, Int. Ed. Engl.*, 1995, 34, 1348; J. F. Hartwig, *Synlett*, 1997, 329; J. F. Hartwig, *Pure Appl. Chem.*, 1999, 71, 1417-1423; S. L. MacNeil et al., *Synlett*, 1998, 419; J. F. Hartwig, Angew, *Chem. Int. Ed. Engl.*, 1998, 37, 2046-2067; J. F. Hartwig, *Acc. Chem. Res.*, 1998, 31, 852; J. P. Wolfe, et al., *Acc. Chem. Res.*, 1998, 31, 805-818; B. H. Yang and S. L. Buchwald, *J. Organomet. Chem.*, 1999, 576 (1-2), 125-146; S. L. Buch wald, *Top. Curr. Chem.*, 2002, 219, 131-209; J. F. Hartwig, "Palladium-catalyzed amination of aryl halides and related reactions" in "Handbook of Organopalladium Chemistry for Organic Synthesis" by E.-i. Negishi, et al., Wiley-Interscience (2002), pp. 1051-1096; L. Jiang and S. L. Buchwald, "Palladium-Catalyzed Aromatic Carbon-Nitrogen Bond Formation" in "Metal-Catalyzed Cross-Coupling Reactions" by A. de Meijere, et al., Wiley-VCH (2004), pp. 699-760; U.S. Pat. No. 5,576,460; U.S. Pat. No. 5,977,361; and U.S. Pat. No. 6,235,938. The catalyzed amination reaction is believed to involve a catalytic cycle involving oxidative addition of the aromatic compound to a palladium (0) complex, ligand exchange wherein the leaving group of the aromatic compound is exchanged for the amine to form a palladium-nitrogen complex, followed by reductive elimination of the aromatic amine compound.

In spite of the advance represented by the catalyzed cross-coupling reaction of substituted aromatic compounds with amino compounds, a significant limitation of the process is that prior to the present invention, no method for directly cross-coupling ammonia or metal amides (containing an NH$_2^-$ anion) with an aromatic compound to form aromatic primary amines has been reported. Such a method, if available, would be a very convenient method of preparing aromatic primary amines, particularly in view of the fact that ammonia is a very readily available, and cheap, bulk chemical.

Instead of using ammonia, previous syntheses of aromatic primary amines using the cross-coupling methodology have employed ammonia surrogates that require deprotection in order to give the primary amine. Such approaches thus give the primary amine only indirectly. Examples of references describing such approaches using ammonia surrogates are: S. Jaime-Figueroa, et al., *Tetrahedron Lett.* 1998, 39, 1313; G. Mann, et al., *J. Am. Chem. Soc.,* 1998, 120, 827; J. P. Wolfe, et al., *Tetrahedron Lett.,* 1997, 38, 6367; J. P. Wolfe, et al., *J. Org. Chem.,* 2000, 65, 1158; G. A. Grasa, et al., *J. Org. Chem.,* 2001, 66, 7729; S. Lee, et al., *Org. Lett.,* 2001, 3, 2729; X. Huang, et al., *Org. Lett.,* 2001, 3, 3417; J. Barluenga, et al., *Angew. Chem., Int. Ed. Engl.,* 2004, 43, 343. Jaime-Figueroa, et al. (*Tetrahedron Lett.,* 1998, 39, 1313-1316) described the use of allyl amines as ammonia equivalents in the cross-coupling methodology, in a process that required subsequent deallylation of the resulting allylamine to prepare the desired primary amine. Wolfe, et al. (*Tetrahedron Lett.,* 1997, 38, 6368) described the use of benzophenone imine as an ammonia surrogate in cross-coupling reactions in which the cross-coupling proceeds initially to give an N-substituted benzophenone imine, which undergoes acid-catalyzed hydrolysis to give the desired aromatic primary amine. In another approach, lithium hexamethyldisilazide has been used in cross-coupling reactions, with the resulting aromatic N,N-bis(trimethylsilyl)amine yielding the aromatic primary amine upon hydrolysis. S. Lee, et al., *Org. Lett.,* 2001, 3, 2729; X. Huang, et al., *Org. Lett.,* 2001, 3, 3417.

In view of the disadvantages of traditional methods of synthesizing aromatic primary amines, and the convenience and efficiency of the transition-metal-catalyzed cross-coupling reactions to form amines, it would be very desirable to have available a process in which cross-coupling of ammonia or a metal amide could be used in a cross-coupling reaction to prepare primary amines directly, without having to use ammonia surrogates.

Such a reaction would be useful for the synthesis of a wide variety of compounds. Compounds that could be prepared by such a process include compounds that are useful, for example, as pharmaceuticals, agricultural products (e.g., herbicides, pesticides), organic materials such as anti-oxidants, or ligands for use in catalysts, as well as intermediates in the synthesis of such products.

SUMMARY OF THE INVENTION

In one aspect of the invention, a process is provided for preparing an aromatic primary amine, said aromatic primary amine comprising an amino group attached to an aromatic ring, said process comprising reacting:
(a) an arylating agent comprising a leaving group attached to an aromatic ring; and
(b) an ammoniating agent selected from the group consisting of:
(i) ammonia; and
(ii) a metal amide;

in a composition comprising a complex comprising:
(a) a Group VIII metal atom or ion; and
(b) a ligand, wherein the ligand is a compound of formula I:

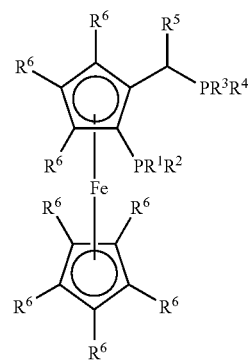

wherein:
R$^1$ and R$^2$ are independently selected from the group consisting of (C$_1$-C$_{12}$)alkyl, (C$_1$-C$_{12}$)heteroalkyl, and optionally substituted aromatic rings, or —PR$^1$R$^2$ is a radical of the formula II:

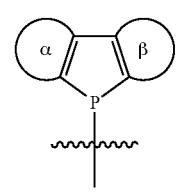

wherein α and β are optionally substituted aromatic rings;
R$^3$ and R$^4$ are independently selected from the group consisting of (C$_1$-C$_{12}$)alkyl, (C$_1$-C$_{12}$)heteroalkyl, and optionally substituted aromatic rings, or —PR$^3$R$^4$ is a radical of the formula II;
R$^5$ is selected from the group consisting of hydrogen, (C$_1$-C$_8$)alkyl, (C$_1$-C$_8$)heteroalkyl and optionally substituted aromatic rings,
each R$^6$ is independently selected from the group consisting of hydrogen, and (C$_1$-C$_4$)alkyl;
wherein each of said optionally substituted aromatic rings is either unsubstituted or substituted at any substitutable position with one or more substituents independently selected from the group consisting of (C$_1$-C$_4$)alkyl, (C$_1$-C$_4$)heteroalkyl, (C$_1$-C$_3$) fluorinated alkyl, —OR$^7$, —SR$^7$, and NR$^7{}_2$;
each R$^7$ is independently selected from the group consisting of (C$_1$-C$_4$)alkyl and (C$_1$-C$_4$)heteroalkyl, or, within any occurrence of NR$^7{}_2$, independently of any other occurrence of NR$^7{}_2$ the two R$^7$ groups in combination form (C$_4$-C$_8$)alkylene or (C$_4$-C$_8$)heteroalkylene;
or any one occurrence of R$^6$, or any one substitutable position of any one of the groups R$^1$, R$^2$, R$^3$, R$^4$, R$^5$ and R$^7$, is a point of attachment, directly or via a tethering group, to a polymer or a solid phase support;
provided that when the ammoniating agent is ammonia, the composition comprising the complex further comprises a base;

whereby the leaving group of the arylating agent is substituted by an amino group to form the aromatic primary amine.

Another aspect of the invention relates to compositions that are useful as reagents for the synthesis of aromatic primary amines. In this aspect of the invention, a composition is provided, said composition comprising:
(a) an ammoniating agent selected from the group consisting of:
  (i) ammonia; and
  (ii) a metal amide; and
(b) a complex comprising:
  (i) a Group VIII metal atom or ion; and
  (ii) a ligand, wherein the ligand is a compound of formula I:

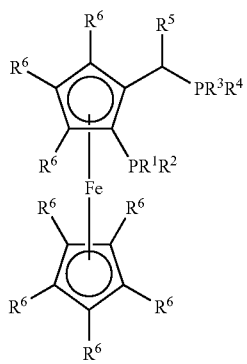

(I)

wherein:
$R^1$ and $R^2$ are independently selected from the group consisting of $(C_1-C_{12})$alkyl, $(C_1-C_{12})$heteroalkyl, and optionally substituted aromatic rings, or —$PR^1R^2$ is a radical of the formula II:

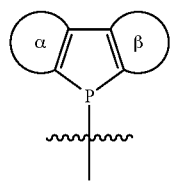

(II)

wherein α and β are optionally substituted aromatic rings;
$R^3$ and $R^4$ are independently selected from the group consisting of $(C_1-C_{12})$alkyl, $(C_1-C_{12})$heteroalkyl, and optionally substituted aromatic rings, or —$PR^3R^4$ is a radical of the formula II;
$R^5$ is selected from the group consisting of hydrogen, $(C_1-C_8)$alkyl, $(C_1-C_8)$heteroalkyl and optionally substituted aromatic rings,
each $R^6$ is independently selected from the group consisting of hydrogen, and $(C_1-C_4)$alkyl;
wherein each of said optionally substituted aromatic rings is either unsubstituted or substituted at any substitutable position with one or more substituents independently selected from the group consisting of $(C_1-C_4)$alkyl, $(C_1-C_4)$heteroalkyl, $(C_1-C_3)$ fluorinated alkyl, —$OR^7$, —$SR^7$, and $NR^7_2$;
each $R^7$ is independently selected from the group consisting of $(C_1-C_4)$alkyl and $(C_1-C_4)$heteroalkyl, or, within any occurrence of $NR^7_2$, independently of any other occurrence of $NR^7_2$ the two $R^7$ groups in combination form $(C_4-C_8)$alkylene or $(C_4-C_8)$heteroalkylene;
or any one occurrence of $R^6$, or any one substitutable position of any one of the groups $R^1$, $R^2$, $R^3$, $R^4$, $R^5$ and $R^7$, is a point of attachment, directly or via a tethering group, to a polymer or a solid phase support;
provided that when the ammoniating agent is ammonia, the composition further comprises a base.

As a further aspect of the invention, there is provided a transition metal complex according to the formula IV:

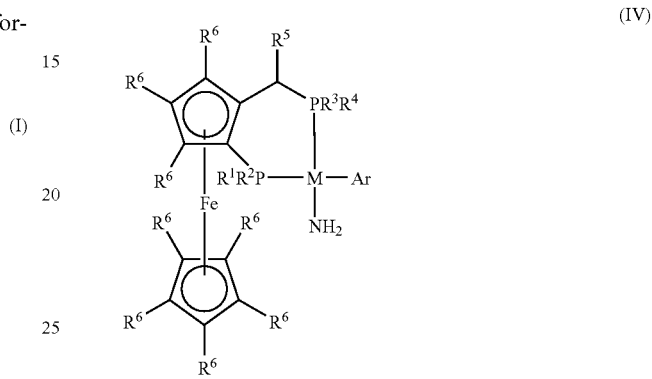

(IV)

wherein:
M comprises a Group VIII metal atom or ion;
Ar represents a moiety comprising an aromatic ring wherein a carbon atom of the aromatic ring is sigma-bonded to the Group VIII metal atom or ion of M;
$R^1$ and $R^2$ are independently selected from the group consisting of $(C_1-C_{12})$alkyl, $(C_1-C_{12})$heteroalkyl, and optionally substituted aromatic rings, or —$PR^1R^2$ is a radical of the formula II:

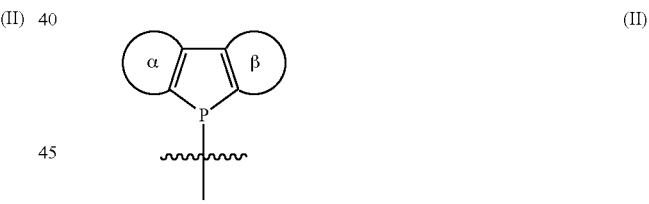

(II)

wherein α and β are optionally substituted aromatic rings;
$R^3$ and $R^4$ are independently selected from the group consisting of $(C_1-C_{12})$alkyl, $(C_1-C_{12})$heteroalkyl, and optionally substituted aromatic rings, or —$PR^3R^4$ is a radical of the formula II;
$R^5$ is selected from the group consisting of hydrogen, $(C_1-C_8)$alkyl, $(C_1-C_8)$heteroalkyl and optionally substituted aromatic rings,
each $R^6$ is independently selected from the group consisting of hydrogen, and $(C_1-C_4)$alkyl;
wherein each of said optionally substituted aromatic rings is either unsubstituted or substituted at any substitutable position with one or more substituents independently selected from the group consisting of $(C_1-C_4)$alkyl, $(C_1-C_4)$heteroalkyl, $(C_1-C_3)$ fluorinated alkyl, —$OR^7$, —$SR^7$, and $NR^7_2$;
each $R^7$ is independently selected from the group consisting of $(C_1-C_4)$alkyl and $(C_1-C_4)$heteroalkyl, or, within any occurrence of $NR^7_2$, independently of any other occurrence of $NR^7_2$ the two $R^7$ groups in combination form $(C_4-C_8)$alkylene or $(C_4-C_8)$heteroalkylene;

or any one occurrence of $R^6$, or any one substitutable position of any one of the groups $R^1$, $R^2$, $R^3$, $R^4$, $R^5$ and $R^7$, is a point of attachment, directly or via a tethering group, to a polymer or a solid phase support.

DETAILED DESCRIPTION OF THE INVENTION

As used herein, the singular forms "a," "an" and "the" include plural referents unless the context clearly dictates otherwise.

The inventors have discovered a novel catalytic process of preparing aromatic primary amines from the reaction of a suitable arylating agent with ammonia or a metal amide. In the process of the invention, the reaction generally forms the primary aromatic amine as the major reaction product. The process is catalyzed by a Group VIII metal complex such as a palladium complex that is either isolated or generated in situ.

As an aspect of the invention, there is provided a process for synthesizing an aromatic primary amine from the reaction of an arylating agent and the combination of ammonia and a base catalyzed by a Group VIII metal. As another aspect of the invention, there is provided a process for synthesizing an aromatic primary amine from the reaction of an arylating agent and the combination of ammonia and a base catalyzed by a complex of palladium. As another aspect of the invention, there is provided a process for synthesizing an aromatic primary amine from the reaction of an arylating agent and the combination of ammonia and a base catalyzed by a complex of palladium ligated by a phosphine or N-heterocyclic carbene ligand. In a particular embodiment thereof, the complex of palladium is ligated by a phosphine of formula I, as described below, or any of the embodiments thereof, as herein described.

As a further aspect of the invention, there is provided a process for synthesizing an aromatic primary amine from the reaction of an arylating agent and an alkali metal amide catalyzed by a Group VIII metal. As another aspect of the invention, there is provided a process for synthesizing an aromatic primary amine from the reaction of an arylating agent and an alkali metal amide catalyzed by a complex of palladium. As another aspect of the invention, there is provided a process for synthesizing an aromatic primary amine from the reaction of an arylating agent and an alkali metal amide catalyzed by a complex of palladium ligated by a phosphine or N-heterocyclic carbene ligand. In a particular embodiment thereof, the complex of palladium is ligated by a phosphine of formula I, as described below, or any of the embodiments thereof, as herein described.

In one aspect of the invention, a process is provided for preparing an aromatic primary amine, said aromatic primary amine comprising an amino group attached to an aromatic ring, said process comprising reacting:

(a) an arylating agent comprising a leaving group attached to an aromatic ring; and
(b) an ammoniating agent selected from the group consisting of:
  (i) ammonia; and
  (ii) a metal amide;
in a composition comprising a complex comprising:
(a) a Group VIII metal atom or ion; and
(b) a ligand, wherein the ligand is a compound of formula I:

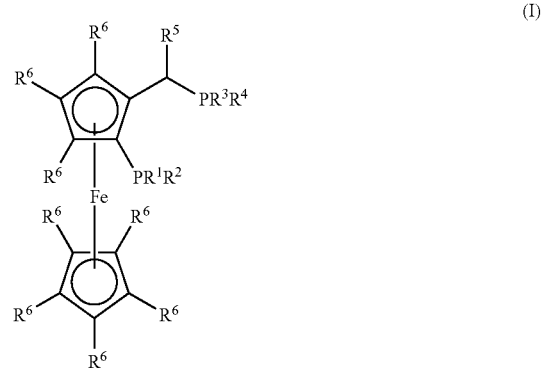

wherein:
$R^1$ and $R^2$ are independently selected from the group consisting of $(C_1-C_{12})$alkyl, $(C_1-C_{12})$heteroalkyl, and optionally substituted aromatic rings, or —$PR^1R^2$ is a radical of the formula II:

wherein α and β are optionally substituted aromatic rings;
$R^3$ and $R^4$ are independently selected from the group consisting of $(C_1-C_{12})$alkyl, $(C_1-C_{12})$heteroalkyl, and optionally substituted aromatic rings, or —$PR^3R^4$ is a radical of the formula II;
$R^5$ is selected from the group consisting of hydrogen, $(C_1-C_8)$alkyl, $(C_1-C_8)$heteroalkyl and optionally substituted aromatic rings,
each $R^6$ is independently selected from the group consisting of hydrogen, and $(C_1-C_4)$alkyl;
wherein each of said optionally substituted aromatic rings is either unsubstituted or substituted at any substitutable position with one or more substituents independently selected from the group consisting of $(C_1-C_4)$alkyl, $(C_1-C_4)$heteroalkyl, $(C_1-C_3)$ fluorinated alkyl, —$OR^7$, —$SR^7$, and $NR^7_2$;
each $R^7$ is independently selected from the group consisting of $(C_1-C_4)$alkyl and $(C_1-C_4)$heteroalkyl, or, within any occurrence of $NR^7_2$, independently of any other occurrence of $NR^7_2$ the two $R^7$ groups in combination form $(C_4-C_8)$alkylene or $(C_4-C_8)$heteroalkylene;
or any one occurrence of $R^6$, or any one substitutable position of any one of the groups $R^1$, $R^2$, $R^3$, $R^4$, $R^5$ and $R^7$, is a point of attachment, directly or via a tethering group, to a polymer or a solid phase support;

provided that when the ammoniating agent is ammonia, the composition comprising the complex further comprises a base;

whereby the leaving group of the arylating agent is substituted by an amino group to form the aromatic primary amine.

The term "aromatic primary amine" as used herein means a compound comprising an amino group (i.e. —$NH_2$) attached by a single bond to an aromatic ring.

The term "aromatic compound" as used herein means a compound having one or more polyunsaturated carbocyclic or heterocyclic rings having aromatic character, characterized by having 4n+2 pi electrons (where n is an integer). The term "aromatic ring" describes individual polyunsaturated carbocyclic or heterocyclic rings within such a compound. Commonly, aromatic compounds comprise 6-membered carbocyclic or heterocyclic rings (the heterocyclic rings containing nitrogen as the heteroatom) and/or 5-membered heterocyclic rings (the heterocyclic rings containing nitrogen, oxygen, and/or sulfur as the heteroatom). The aromatic compounds may contain one or more aromatic rings which may be pendant (as in biphenyl) or fused (as in naphthylene). Examples of carbocyclic aromatic ring systems which may occur in aromatic compounds include benzene rings. Examples of heterocyclic ring systems that may occur in aromatic compounds include pyridine, pyrazine, pyrimidine, pyridazine, thiophene, furan, pyrrole, imidazole, thiazole, oxazole, pyrazole, isothiazole, 1,2,3-triazole, 1,2,4-triazole, 1,3,4-triazole, 1,2,3-thiadiazole, 1,2,3-oxadiazole, 1,3,4-thiadiazole and 1,3,4-oxadiazole rings. Examples of polycyclic ring systems that may occur within aromatic compounds include naphthalene, indole, quinoline, isoquinoline, cinnoline, quinoxaline, 1,4-benzodioxane, benzofuran, benzisoxazole, benzothiophene, benzoxazole, benzothiazole, purine, benzimidazole, benzotriazole, carbazole, carboline, and acridine.

"Leaving group" means a univalent group (—X) attached to an aromatic ring which, when attached to hydrogen, is an acid (H—X) with a $pK_a$ of about 5 or lower, or, in the case of preferred leaving groups, a $pK_a$ of about 2 or lower. Thus, a leaving group is a compound which in an aromatic substitution may be expelled to give, typically, a stable anion. Examples of leaving groups include halogen, for example chloride, bromide, and iodide, and sulfonate groups, for example trifluoromethanesulfonate (—OTf), arenesulfonates (such as phenylsulfonate, p-toluenesulfonate (—OTs), and naphthalenesulfonate), or alkanesulfonates (such as mesylate). The preferred leaving groups are halogen, particularly bromine.

The term "arylating agent" as used herein means a reagent that comprises a leaving group attached to an aromatic ring. In the process of the invention, the arylating agent provides the aromatic ring portion of the aromatic primary amine formed.

In the process of the invention, the amino group of the aromatic primary amine formed is provided either by ammonia or by a metal amide.

When ammonia is used as the source of the amino group, a base is included in the reaction composition. Suitable bases are those wherein the base's conjugate acid has a pKa of about 9 or greater, preferably about 12 or greater. Examples of suitable bases include alkali metal alkoxides, particularly tertiary alkoxides, for example t-butoxides. Preferred alkoxides include sodium t-butoxide and potassium t-butoxide. Sodium t-butoxide is most preferred. Other suitable bases include alkali metal carbonates, for example sodium, potassium, or cesium carbonate. Cesium carbonate is preferred. Other suitable bases include alkali metal phosphates, for example tribasic potassium phosphate. Other suitable bases include alkali metal hydroxides, for example sodium hydroxide. Other suitable bases include metal amides, for example alkali metal amides. In addition to metal amides containing an unsubstituted amide moiety ($NH_2$—), substituted amides such as dialkylamides may usefully be used as bases in the process of the invention so long as such amides or the conditions of the reaction are selected (e.g. by the use of sterically hindered amides) such that an amination reaction by the substituted amide (to give a secondary or tertiary amine) does not compete significantly with the formation of the aromatic primary amine. If a metal amide is used as the base, then the use of a metal amide containing an unsubstituted amide moiety ($NH_2$—), for example an alkali metal amide such as lithium amide ($LiNH_2$), is preferred. The person skilled in the art will know how to select a suitable base for a given application. Factors in selecting the base include compatibility with other functional groups that may be present in the arylating agent, and the solubility of the base in the solvent selected for the reaction.

The ammonia used in the reaction may be provided in the any suitable form. For example, gaseous ammonia may be introduced into the reaction vessel, which optionally may be pressurized with ammonia or a mixture of ammonia and one or more other gases. Alternatively, the ammonia may be pre-dissolved in a solvent and introduced into the reaction vessel in the form of a solution. As another alternative, the ammonia may be generated in situ from the reaction of an ammonium salt with a base. For convenience, the base used in forming ammonia from the ammonium salt may also serve as the base required in the reaction composition when ammonia is used as the source of the amino group.

In the reactions using ammonia and a base as the ammoniating agent, generally at least one equivalent of both ammonia and the base are used to drive the reaction to completion (in the sense of converting all of the arylating agent to the aromatic primary amine). An excess of ammonia is preferred in order to promote the formation of the primary amine over formation of secondary and/or tertiary amines (in which more than one molecule of the arylating agent reacts with a given ammonia molecule). Generally an equivalent amount, or relatively small excess (up to about 5-fold) of the base over the arylating agent, is used (although this is preferred to avoid waste and facilitate isolation of pure product rather than being critical to the success of the process).

As an alternative to using ammonia as the source of the amino group in the reaction, a metal amide may be used as the ammoniating agent. As used herein, the term "metal amide" means a metal compound formally containing a metal cation and an amide anion ($NH_2$—). The person skilled in the art will appreciate that the definition encompasses compounds containing discrete amide anions as well as compounds having an $NH_2$ group with partial anionic character bound or coordinated to a metal atom having partial cationic character. Examples include alkali metal amides, for example lithium amide, sodium amide, and potassium amide. Lithium amide is preferred.

When the metal amide is an alkali metal amide, reagents that are conventionally used to modify the reactivity of alkali metal agents may be helpful in optimizing the reaction conditions for any particular substrate. Examples of such reagents include complexing agents that bind the alkali metal ion, for example crown ethers, or other chelating agents such as diamine ligands, for example tetramethylethylenediamine (TMEDA).

Amides may also be formed in situ by ligand exchange reactions, for example by the reaction of a metal amide, for example an alkali metal amide, with a salt, for example a halide, of another metal. For example, a zinc species formed by the reaction of an alkali metal amide, for example lithium amide, with a zinc halide, for example zinc chloride, may be advantageously used, for example as demonstrated in Example 29. Thus, as a further aspect of the invention, there is provided a process wherein the reaction of the arylating agent with the metal amide is performed in a composition comprising a metal halide. In a particular sub-embodiment of this aspect of the invention, the metal amide is an alkali metal amide, preferably lithium amide, and the metal halide is a zinc halide, preferably zinc chloride. In the context of this particular aspect of the invention, when it is said that the composition comprises the metal halide, it is meant that the composition comprises the product formed by the process of mixing the metal halide with the other components of the reaction mixture, and this aspect of the invention is therefore not intended to be limited by the exact nature of the resulting species. Similarly a composition comprising zinc halide or zinc chloride is intended to mean that the product formed by the process of mixing the zinc halide (or chloride) into the reaction mixture is present in the composition. While not being limited by any theory, it is believed that the actual species present is a zinc amide species. A preferred embodiment of this aspect of the invention is an ammoniating composition comprising an alkali metal amide, preferably lithium amide, a zinc halide, preferably zinc chloride, and an alkali metal chelating agent, particularly tetramethylethylenediamine.

The process of the invention is catalyzed by an organometallic catalyst. The catalyst comprises composition comprising a Group VIII metal atom or ion and a ligand according to formula I. While not being limited by theory, it is believed that the catalyst is a coordination complex wherein the ligand coordinates to the metal. The catalytic complex may either be pre-formed or may be formed in situ by introducing the metal and ligand separately into the composition.

The term "Group VIII metal" means a metal selected from the group consisting of iron, cobalt, nickel, ruthenium, rhodium, palladium, osmium, iridium, and platinum. The preferred Group VIII metals are palladium, platinum, and nickel. Palladium is most preferred. The Group VIII metal may exist in any oxidation state ranging from the zero-valent state to any higher valence available to the metal. Since the catalytic cycle is believed to involve changes of oxidation state, complexes involving more than one oxidation state of the metal may be present in the solution during the course of the reaction. For example palladium (0) and palladium (II) complexes are believed to be involved in the catalytic cycle involving palladium.

The ligand that has been found to be useful in the process of the invention is the compound according to formula I. Ligands according to formula I have been described in the literature, for example in U.S. Pat. Nos. 5,466,844; 5,565,594; and 5,563,308; the entire disclosures of which are incorporated herein by reference. In the following, the terms used in defining the ligands according to formula I, are explained, and the ligands used in preferred embodiments of the invention are disclosed.

The term "$(C_x-C_y)$alkyl" (wherein x and y are integers) refers to an alkyl group containing between x and y carbon atoms. An alkyl group formally corresponds to an alkane with one C—H bond replaced by the point of attachment of the alkyl group to the remainder of the compound. An alkyl group may be straight-chained or branched. Alkyl groups having 5 or more carbon atoms may be cyclic. Cyclic alkyl groups having 7 or more carbon atoms may contain more than one ring and be polycyclic. Examples of straight-chained alkyl groups include methyl, ethyl, n-propyl, n-butyl, and n-octyl. Examples of branched alkyl groups include i-propyl, t-butyl, and 2,2-dimethylethyl. Examples of cyclic alkyl groups include cyclopentyl, cyclohexyl, cyclohexylmethyl, and 4-methylcyclohexyl. Examples of polycyclic alkyl groups include bicyclo[2.2.1]heptanyl, norbornyl, and adamantyl The term "$(C_x-C_y)$alkylene" (wherein x and y are integers) refers to an alkylene group containing between x and y carbon atoms. An alkylene group formally corresponds to an alkane with two C—H bond replaced by points of attachment of the alkylene group to the remainder of the compound.

The term "$(C_x-C_y)$heteroalkyl" (wherein x and y are integers) refers to a side-chain having between x and y carbon atoms connected via carbon and containing one or more atoms selected from the group consisting of oxygen, sulfur, and nitrogen. The $(C_x-C_y)$heteroalkyl group formally corresponds to an alkyl group wherein nitrogen has been substituted for a methine group, oxygen has been substituted for a methylene group, and/or sulfur has been substituted for a methylene group. Preferred $(C_x-C_y)$heteroalkyl groups are those having one heteroatom, but if two or more heteroatoms are present, a chain of at least two carbon atoms preferably separates each pair of heteroatoms so that any carbon atom has a bond to at most one heteroatom. Preferably, oxygen and sulfur atoms in a heteroalkyl group each are bonded to at least two carbon atoms (i.e. are ether or thioether groups respectively), and nitrogen is bonded to three carbon atoms (i.e. is a tertiary amine group). $(C_x-C_y)$heteroalkyl groups may be straight-chained or branched. $(C_x-C_y)$heteroalkyl groups having a total of at least five carbon and heteroatoms may also be cyclic. Examples of heteroalkyl groups containing oxygen are methoxymethyl, ethoxymethyl, and 2-tetrahydrofuranyl. An example of a heteroalkyl group containing sulfur is methylthiomethyl. Examples of heteroalkyl groups containing nitrogen are dimethylaminomethyl, and dimethylaminoethyl.

The term "$(C_x-C_y)$heteroalkylene" (wherein x and y are integers) refers to a side-chain having between x and y carbon atoms connected via carbon and containing one atom selected from the group consisting of oxygen, sulfur, and nitrogen. The $(C_x-C_y)$heteroalkylene group formally corresponds to an alkylene group wherein nitrogen has been substituted for a methine group, oxygen has been substituted for a methylene group, and/or sulfur has been substituted for a methylene group. When the $(C_x-C_y)$heteroalkylene group is connected to a heteroatom, a chain of at least two carbon atoms separates that heteroatom from the heteroatom within the heteroalkene group. Preferably, oxygen and sulfur atoms in a heteroalkyl group each are bonded to at least two carbon atoms (i.e. ether or thioether groups respectively), and nitrogen is bonded to three carbon atoms (i.e. is a tertiary amine group). Examples of heteroalkene groups are —$CH_2CH_2OCH_2CH_2$—, —$CH_2CH_2N(Me)CH_2CH_2$—, and —$CH_2CH_2SCH_2CH_2$—.

The term "$(C_x-C_y)$ fluorinated alkyl" (wherein x and y are integers) refers to an alkyl group having between x and y carbon atoms wherein at least one C—H bond is substituted by a C—F bond. Preferred fluorinated alkyl groups contain at least one $CF_2$ group or $CF_3$ group or both. Other preferred fluorinated alkyl groups are perfluoroalkyl groups in which all C—H bonds are substituted by fluorine. Examples of perfluoroalkyl groups include trifluoromethyl, 2,2,2-trifluoroethyl, 1,1-difluoroethyl, pentafluoroethyl, and perfluoropropyl.

$R^1$, $R^2$, $R^3$ and $R^4$ are preferably $(C_1-C_{12})$alkyl or optionally substituted phenyl.

When $R^1$, $R^2$, $R^3$ or $R^4$ are acyclic $(C_1-C_{12})$alkyl, they preferably contain 1 to 8, more preferably 1 to 4, carbon atoms. Typical examples are methyl, ethyl, n- and i-propyl, n-, i- and t-butyl, pentyl, hexyl, heptyl, octyl nonyl, decyl, undecyl and dodecyl. Methyl, ethyl, n- and i-propyl, n-, i- and t-butyl are preferred.

When $R^1$, $R^2$, $R^3$ or $R^4$ are cyclic $(C_5-C_{12})$alkyl, they preferably contain 5 to 8, most preferably 5 or 6, ring carbon atoms. Exemplary of cycloalkyl are cyclopentyl, cyclohexyl, cycloheptyl, cyclooctyl, cyclodecyl and cyclododecyl. Cyclopentyl and cyclohexyl are preferred and cyclohexyl is especially preferred.

When $R^1$, $R^2$, $R^3$ or $R^4$ are optionally substituted aromatic rings, they preferably are furyl or phenyl, more preferably phenyl, and preferably have 1 or 2 substituents, or, more preferably, are unsubstituted.

The aromatic rings α and β are each preferably phenyl rings, and preferably are unsubstituted.

$R^5$ is preferably hydrogen or $(C_1-C_8)$alkyl, preferably hydrogen or $(C_1-C_4)$alkyl, and when alkyl, is preferably methyl and ethyl.

$R^6$ is preferably hydrogen. $R^6$ is preferably other than hydrogen at five or fewer occurrences in formula I, more preferably four or fewer, more preferably three or fewer, more preferably two or fewer, more preferably one or fewer occurrences. Most preferably, $R^6$ is hydrogen at every occurrence in formula I.

$R^7$ is preferably $(C_1-C_4)$alkyl, preferably methyl.

In particular embodiments of the invention, each of $R^1$, $R^2$, $R^3$ and $R^4$ is $(C_1-C_{12})$alkyl, preferably $(C_3-C_8)$alkyl, and, more preferably, secondary or tertiary $(C_3-C_8)$alkyl.

In preferred embodiments of the invention, each of $R^1$ and $R^2$ is independently optionally substituted phenyl or secondary or tertiary alkyl, more preferably optionally substituted, preferably unsubstituted, phenyl or secondary cyclic alkyl and is particularly preferably unsubstituted phenyl or cyclohexyl.

In these and other preferred embodiments of the invention, each of $R^3$ and $R^4$ is independently secondary or tertiary alkyl, more preferably tertiary alkyl and particularly preferably t-butyl.

In other preferred embodiments of the invention, $R^1$ and $R^2$ are identical to each other and $R^3$ and $R^4$ are identical to each other. In preferred sub-embodiments thereof, $R^1$ and $R^2$ are identical to each other, and are phenyl or $(C_3-C_8)$alkyl, preferably phenyl or secondary or tertiary $(C_3-C_8)$alkyl, more preferably phenyl or secondary cyclic alkyl, and $R^3$ and $R^4$ are identical to each other, and are $(C_3-C_8)$alkyl, preferably secondary or tertiary $(C_3-C_8)$alkyl. In more preferred sub-embodiments thereof, $R^1$ and $R^2$ are identical to each other, and are secondary $(C_3-C_8)$alkyl, preferably cyclic secondary $(C_5-C_8)$alkyl, $R^3$ and $R^4$ are identical to each other, and are tertiary $(C_3-C_8)$alkyl. In preferred embodiments, $R^1$ and $R^2$ are identical to each other and are selected from the group consisting of phenyl, i-propyl, cyclopentyl, cyclohexyl, cyclopentyl, t-butyl, preferably or cyclohexyl; and $R^3$ and $R^4$ are identical to each other and are selected from the group consisting of i-propyl, cyclopentyl, cyclohexyl, cyclopentyl and t-butyl, preferably t-butyl. For each of these embodiments and sub-embodiments, yet other sub-embodiments thereof are those wherein $R^5$ is hydrogen or $(C_1-C_8)$alkyl, preferably hydrogen or $(C_1-C_4)$alkyl, and when alkyl, is preferably methyl and ethyl. For each of all of these embodiments and sub-embodiments, yet other sub-embodiments thereof are those wherein $R^6$ is hydrogen.

The terms "secondary" and "tertiary" used to describe alkyl groups are familiar to the person skilled in the art, and describe the substitution pattern at the attachment point of the alkyl group. In a "secondary" alkyl group, the alkyl group is attached via a carbon having one bond to hydrogen and two bonds to other carbon atoms. Examples include i-propyl, i-butyl, cyclopentyl, and cyclohexyl. In "tertiary" alkyl group, the alkyl group is attached via a carbon atom that has three bonds to other carbon atoms. Examples include t-butyl and 1-methyl-1-cyclohexyl.

The ligands of formula I may exist in diastereoisomeric or enantiomeric forms. In particular, the ligands of formula I are chiral since the two faces of the cyclopentadienyl ring bearing the phosphine substituents are enantiotopic so that binding of the iron to the different faces results in different enantiomers. Indeed, chiral ligands of the formula I are known in the art, and have been used in asymmetric catalysis. However, in the process of the present invention, it is not believed that the stereochemistry of the ligand is critical to its usefulness. The person skilled in the art will appreciate that the process of the invention involves aromatic substitution at a reaction center that is not itself chiral, so that in general it is expected that either enantiomer of the ligand of formula I, or a mixture thereof, including the racemate, will be effective in the process of the invention. For particular applications, for example where the arylating agent is itself chiral, it may be advantageous to use one or other enantiomer of the compounds of formula I.

The stereochemistry of the compounds of formula I are named by designating the stereochemistry of each chiral center according to the Cahn-Ingold-Prelog system. A chiral center is a carbon atom having four different substituents. The isomers resulting from the presence of a chiral center comprise a pair of non-superimposable isomers that are called "enantiomers." Single enantiomers of a pure compound are optically active, i.e., they are capable of rotating the plane of plane polarized light. *Advanced Organic Chemistry*, Jerry March, John 4$^{th}$ Edition (Wiley 1992), p. 109. Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). In the example shown in Scheme 2 below, the Cahn-Ingold-Prelog ranking is A>B>C>D. The lowest ranking atom, D is oriented away from the viewer.

Scheme 1

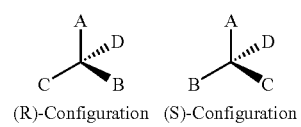

(R)-Configuration  (S)-Configuration

The chirality results of a substituted ferrocene from the presence of a "chiral plane" rather than a chiral center. Conventionally, however, the stereochemistry of ferrocene (a metallocene), such as, is designated by conceptually regarding the metal atom of the ferrocene as being sigma bonded to each carbon of the η$^5$-bonded cyclopentadienyl ring, such that each carbon of the cyclopentadienyl ring is regarded as a chiral center. The chirality of the complex is then designated determining the highest ranked carbon atom of the cyclopentadienyl ring (using the Cahn-Ingold-Prelog system) a stereochemistry assigning its stereochemistry as if it were a chiral center. *Stereochemistry of Organic Compounds* by Ernest L. Eliel, et al., (Wiley 1994), pp. 1119-22; K. Schlögl, *Top. Stereochem.*, 1967, 1, 39.

The phosphine ligands that are useful in the process the invention are commercially available, known in the literature, and/or may be prepared by processes that would be known to the person skilled in the art. The person skilled in the art can readily adapt the procedures described in the literature to the synthesis of the required ligands of formula I, drawing from an extremely broad repertoire of synthetic organic reactions that is available to be potentially employed in synthesizing compounds suitable for use in the invention. The person skilled in the art knows how to select and implement appropriate synthetic routes to the phosphine ligands. Suitable synthetic methods may be identified by reference to the literature, including reference sources such as *Comprehensive Organic Synthesis*, Ed. B. M. Trost and I. Fleming (Pergamon Press, 1991), Comprehensive Organic Functional Group Transformations, Ed. A. R. Katritzky, O. Meth-Cohn, and C. W. Rees (Pergamon Press, 1996), *Comprehensive Organic Functional Group Transformations II*, Ed. A. R. Katritzky and R. J. K. Taylor (Editor) (Elsevier, 2$^{nd}$ Edition, 2004), *Comprehensive Heterocyclic Chemistry*, Ed. A. R. Katritzky and C. W. Rees (Pergamon Press, 1984), and *Comprehensive Heterocyclic Chemistry II*, Ed. A. R. Katritzky, C. W. Rees, and E. F. V. Scriven (Pergamon Press, 1996); *The Chemistry of Organophosphorus Compounds*, Volume 1, *Primary, Secondary and Tertiary Phosphines, Polyphosphines and Heterocyclic Organophosphorus* (III) Compounds, Editor: Frank R. Hartley (Wiley, 1990); Ferrocenes: Homogeneous Catalysis/Organic Synthesis/Materials Science, by A. Togni (Wiley-VCH Verlag GmbH, 1995).

Certain ligands of formula I are described, for example, in U.S. Pat. No. 5,466,844; 5,563,308; 5,565,594; and H.-U. Blaser, et al., "Solvias Josiphos Ligands: From Discovery to Technical Applications", *Topics in Catalysis*, 2002, 19, 3-16, the entire disclosures of which are incorporated herein by reference. As described in U.S. Pat. No. 5,466,844, exemplary syntheses of compounds of formula I are by reacting a compound of formula III, wherein L=OAc or $NMe_2$ and $R^1$, $R^2$, $R^3$, $R^4$, $R^5$, and $R^6$ are as defined for formula I, in the presence of an inert solvent, at room temperature or elevated temperature, with a phosphine of formula $HPR^3R^4$, wherein $R^3$ and $R^4$ are as defined for formula I. Such reactions are described in *Bull. Chem. Soc. Jpn.*, 53, 1136-1151. The reaction temperature may be in the range from about 20° C. to about 150° C., preferably from about 40° C. to about 100° C. Suitable solvents are polar protic and aprotic solvents, which may be used singly or as mixtures of two or more solvents. Typical examples of solvents are alkanols such as methanol and ethanol, and carboxylic acids such as formic acid and acetic acid. The compounds of formula I are obtained as racemates, mixtures of stereoisomers or as stereoisomers, depending on whether the compounds of formula III are used as racemates, mixtures of stereoisomers or as stereoisomers. Racemates and mixtures of stereoisomers can be separated by known methods into the stereoisomers, for example by chromatographic methods.

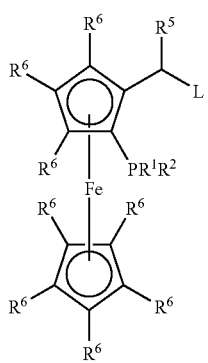

(III)

In particular embodiments of the invention, the ligand of formula I is selected from the group consisting of 1-[2-(bis (3,5-dimethyl-4-methoxyphenyl)-phosphino)ferrocenyl]ethyldicyclohexylphosphine, 1-[2-(bis(4-trifluoromethylphenyl)phosphino)ferrocenyl]ethyl-di-t-butylphosphine; 1-[2-(di(3,5-bis-trifluoromethylphenyl)phosphino)ferrocenyl] ethyldi(3,5-dimethylphenyl)phosphine; 1-[2-(di(3,5-bis-trifluoromethylphenyl)phosphino)-ferrocenyl] ethyldicyclohexylphosphine; 1-[2-(di-(3,5-dimethylphenyl) phosphino)-ferrocenyl]ethylbis(3,5-dimethylphenyl) phosphine; 1-[2-(di-2-furylphosphino)-ferrocenyl]ethyldi-3,5-xylyl phosphine; 1-[2-(dicyclohexylphosphino) ferrocenyl]-ethyldicyclohexylphosphine; 1-[2-(dicyclohexylphosphino)ferrocenyl]-ethyldiphenylphosphine; 1-[2-(dicyclohexylphosphino) ferrocenyl]ethyldi-t-butylphosphine; 1-[2-(diphenylphosphino)ferrocenyl]ethyldi(3,5-dimethylphenyl)-phosphine; 1-[2-(diphenylphosphino) ferrocenyl]ethyldicyclohexylphosphine; 1-[2-(diphenylphosphino)ferrocenyl] ethyldicyclohexylphosphine; 1-[2-(diphenylphosphino) ferrocenyl]ethyldiphenylphosphine; 1-[2-(diphenylphosphino)ferrocenyl]ethyldi-t-butylphosphine; 1-[2-(di-p-tolylphosphino)ferrocenyl]ethyldicyclohexylphosphine; 1-[2-(di-t-butylphosphino)ferrocenyl]ethyldiphenylphosphine; (R)-1-[(S)-2-(bis(3,5-dimethyl-4-methoxyphenyl)phosphino)ferrocenyl] ethyldicyclohexylphosphine; (R)-1-[(S)-2-(bis(4-trifluoromethylphenyl)phosphino)ferrocenyl]ethyl-di-t-butylphosphine; (R)-1-[(S)-2-(di(3,5-bis-trifluoromethylphenyl)phosphino)-ferrocenyl]ethyldi(3,5-dimethylphenyl)phosphine; (R)-1-[(S)-2-(di(3,5-bis-trifluoromethylphenyl)phosphino)ferrocenyl] ethyldicyclohexylphosphine; (R)-1-[(S)-2-(di-(3,5-dimethylphenyl)phosphino)ferrocenyl]ethylbis(3,5-dimethylphenyl)phosphine; (R)-1-[(S)-2-(di-2-furylphosphino)ferrocenyl]ethyldi-3,5-xylyl phosphine; (R)-1-[(S)-2-(dicyclohexylphosphino)ferrocenyl]-ethyldicyclohexylphosphine; (R)-1-[(S)-2-(dicyclohexylphosphino)ferrocenyl]-ethyldiphenylphosphine; (R)-1-[(S)-2-(dicyclohexylphosphino)ferrocenyl]ethyldi-t-butylphosphine; (R)-1-[(S)-2-(diphenylphosphino) ferrocenyl]ethyldi(3,5-dimethylphenyl)phosphine; (R)-1-[(S)-2-(diphenylphosphino)ferrocenyl]-ethyldicyclohexylphosphine; (R)-1-[(S)-2-(diphenylphosphino)ferrocenyl]-ethyldicyclohexylphosphine; (R)-1-[(S)-2-(diphenylphosphino)ferrocenyl]-ethyldiphenylphosphine; (R)-1-[(S)-2-(diphenylphosphino)ferrocenyl]ethyldi-t-butylphosphine; (R)-1-[(S)-2-(di-p-tolylphosphino)ferrocenyl]-ethyldicyclohexylphosphine; (R)-1-[(S)-2-(di-t-butylphosphino)ferrocenyl]-ethyldiphenylphosphine; (S)-1-[(R)-2-(bis(3,5-dimethyl-4-methoxyphenyl)-phosphino) ferrocenyl]ethyldicyclohexylphosphine; (S)-1-[(R)-2-(bis(4-trifluoromethylphenyl)phosphino)ferrocenyl]ethyl-di-t-butylphosphine; (S)-1-[(R)-2-(di(3,5-bis-trifluoromethylphenyl)phosphino)ferrocenyl]ethyldi(3,5-dimethylphenyl)phosphine; (S)-1-[(R)-2-(di(3,5-bis-trifluoromethylphenyl)-phosphino)ferrocenyl] ethyldicyclohexylphosphine; (S)-1-[(R)-2-(di-(3,5-dimethylphenyl)phosphino)ferrocenyl]ethylbis(3,5-dimethylphenyl)phosphine; (S)-1-[(R)-2-(di-2-furylphosphino)ferrocenyl]ethyldi-3,5-xylyl phosphine; (S)-1-[(R)-2-(dicyclohexylphosphino)ferrocenyl] ethyldicyclohexylphosphine; (S)-1-[(R)-2-(dicyclohexylphosphino)ferrocenyl]

ethyldiphenylphosphine; (S)-1-[(R)-2-(dicyclohexylphosphino)ferrocenyl]ethyldi-t-butylphosphine; (S)-1-[(R)-2-(diphenylphosphino)ferrocenyl]ethyldi(3,5-dimethylphenyl)phosphine; (S)-1-[(R)-2-(diphenylphosphino)ferrocenyl]ethyldicyclohexylphosphine; (S)-1-[(R)-2-(diphenylphosphino)ferrocenyl]ethyldicyclohexylphosphine; (S)-1-[(R)-2-(diphenylphosphino)ferrocenyl]ethyldiphenylphosphine; (S)-1-[(R)-2-(diphenylphosphino)ferrocenyl]ethyldi-t-butylphosphine; (S)-1-[(R)-2-(di-p-tolylphosphino)ferrocenyl]ethyldicyclohexylphosphine; and (S)-1-[(R)-2-(di-t-butylphosphino)ferrocenyl]ethyldiphenylphosphine.

In particular embodiments of the invention, the ligand of formula I is selected from the group consisting of [2-(bis(3,5-dimethyl-4-methoxyphenyl)-phosphino)ferrocenyl]methyldicyclohexylphosphine, [2-(bis(4-trifluoromethylphenyl)phosphino)ferrocenyl]methyl-di-t-butylphosphine; [2-(di(3,5-bis-trifluoromethylphenyl)phosphino)ferrocenyl]methyldi(3,5-dimethylphenyl)phosphine; [2-(di(3,5-bis-trifluoromethylphenyl)phosphino)-ferrocenyl]methyldicyclohexylphosphine; [2-(di-(3,5-dimethylphenyl)phosphino)-ferrocenyl]methylbis(3,5-dimethylphenyl)phosphine; [2-(di-2-furylphosphino)-ferrocenyl]ethyldi-3,5-xylyl phosphine; [2-(dicyclohexylphosphino)ferrocenyl]-methyldicyclohexylphosphine; [2-(dicyclohexylphosphino)ferrocenyl]-methyldiphenylphosphine; [2-(dicyclohexylphosphino)ferrocenyl]methyldi-t-butylphosphine; [2-(diphenylphosphino)ferrocenyl]methyldi(3,5-dimethylphenyl)-phosphine; [2-(diphenylphosphino)ferrocenyl]methyldicyclohexylphosphine; [2-(diphenylphosphino)ferrocenyl]methyldicyclohexylphosphine; [2-(diphenylphosphino)ferrocenyl]methyldiphenylphosphine; [2-(diphenylphosphino)ferrocenyl]methyldi-t-butylphosphine; [2-(di-p-tolylphosphino)ferrocenyl]methyldicyclohexylphosphine; [2-(di-t-butylphosphino)ferrocenyl]methyldiphenylphosphine; [(S)-2-(bis(3,5-dimethyl-4-methoxyphenyl)phosphino)ferrocenyl]methyldicyclohexylphosphine; [(S)-2-(bis(4-trifluoromethylphenyl)phosphino)ferrocenyl]methyl-di-t-butylphosphine; [(S)-2-(di(3,5-bis-trifluoromethylphenyl)phosphino)ferrocenyl]methyldi(3,5-dimethylphenyl)phosphine; [(S)-2-(di(3,5-bis-trifluoromethylphenyl)phosphino)-ferrocenyl]methyldicyclohexylphosphine; [(S)-2-(di-(3,5-dimethylphenyl)-phosphino)ferrocenyl]methylbis(3,5-dimethylphenyl)phosphine; [(S)-2-(di-2-furylphosphino)ferrocenyl]methyldi-3,5-xylyl phosphine; [(S)-2-(dicyclohexylphosphino)ferrocenyl]methyldicyclohexylphosphine; [(S)-2-(dicyclohexylphosphino)ferrocenyl]methyldiphenylphosphine; [(S)-2-(dicyclohexylphosphino)ferrocenyl]methyldi-t-butylphosphine; [(S)-2-(diphenylphosphino)ferrocenyl]methyldi(3,5-dimethylphenyl)phosphine; [(S)-2-(diphenylphosphino)ferrocenyl]methyldicyclohexylphosphine; [(S)-2-(diphenylphosphino)ferrocenyl]methyldicyclohexylphosphine; [(S)-2-(diphenylphosphino)ferrocenyl]methyldiphenylphosphine; [(S)-2-(diphenylphosphino)ferrocenyl]methyldi-t-butylphosphine; [(S)-2-(di-p-tolylphosphino)ferrocenyl]methyldicyclohexylphosphine; [(S)-2-(di-t-butylphosphino)ferrocenyl]methyldiphenylphosphine; [(R)-2-(bis(3,5-dimethyl-4-methoxyphenyl)phosphino)ferrocenyl]methyldicyclohexylphosphine; [(R)-2-(bis(4-trifluoromethylphenyl)phosphino)ferrocenyl]methyl-di-t-butylphosphine; [(R)-2-(di(3,5-bis-trifluoromethylphenyl)phosphino)ferrocenyl]methyldi(3,5-dimethylphenyl)phosphine; [(R)-2-(di(3,5-bis-trifluoromethylphenyl)phosphino)-ferrocenyl]methyldicyclohexylphosphine; [(R)-2-(di-(3,5-dimethylphenyl)-phosphino)ferrocenyl]methylbis(3,5-dimethylphenyl)phosphine; [(R)-2-(di-2-furylphosphino)ferrocenyl]methyldi-3,5-xylyl phosphine; [(R)-2-(dicyclohexylphosphino)ferrocenyl]methyldicyclohexylphosphine; [(R)-2-(dicyclohexylphosphino)ferrocenyl]methyldiphenylphosphine; [(R)-2-(dicyclohexylphosphino)ferrocenyl]methyldi-t-butylphosphine; [(R)-2-(diphenylphosphino)ferrocenyl]methyldi(3,5-dimethylphenyl)phosphine; [(R)-2-(diphenylphosphino)ferrocenyl]methyldicyclohexylphosphine; [(R)-2-(diphenylphosphino)ferrocenyl]methyldicyclohexylphosphine; [(R)-2-(diphenylphosphino)ferrocenyl]methyldiphenylphosphine; [(R)-2-(diphenylphosphino)ferrocenyl]methyldi-t-butylphosphine; [(R)-2-(di-p-tolylphosphino)ferrocenyl]methyldicyclohexylphosphine; and [(R)-2-(di-t-butylphosphino)ferrocenyl]methyldiphenylphosphine In preferred embodiments of the invention, the ligand of formula I is selected from the group consisting of 1-[2-(dicyclohexylphosphino)ferrocenyl]-ethyldi-t-butylphosphine; 1-[2-(diphenylphosphino)ferrocenyl]ethyldi-t-butylphosphine; (R)-1-[(S)-2-(dicyclohexylphosphino)ferrocenyl]ethyldi-t-butylphosphine; (R)-1-[(S)-2-(diphenylphosphino)ferrocenyl]ethyldi-t-butylphosphine; (S)-1-[(R)-2-(dicyclohexylphosphino)ferrocenyl]ethyldi-t-butylphosphine; and (S)-1-[(R)-2-(diphenylphosphino)ferrocenyl]ethyldi-t-butylphosphine.

The phosphine ligands of formula I contain two phosphine groups, and therefore potentially chelate the metal. It is not known with certainty whether both, one, or neither phosphorus atoms of the ligand are bound to the transition metal during the entire process of this invention or whether the chelating is in a labile or non-bonded configuration relative to the transition metal during part or all of the process. Generally, it is believed that the ligand is bonded via the phosphorus to the transition metal; but the invention should not be construed as being limited by such a theory. Modern analytical techniques, such as nuclear magnetic resonance spectroscopy ($^{13}C$, $^{1}H$, $^{31}P$), infrared and Raman spectroscopies, and X-ray diffraction, may assist in the determination of initial catalyst structure and changes in structure that occur during the process.

While not wishing to be bound by any theory, it is believed that the catalysts comprising ligands of formula I overcome problems presented by catalysts that are ordinarily used in catalyzed amination reactions. Among the difficulties believed to be presented by the use of ammonia in catalyzed amination reactions are, first, the potential for dative ancillary ligands to be displaced by ammonia to form a catalytically unreactive complex; second, the fact that reductive elimination from an Ar—Pd—NH$_2$ complex has never been observed, possibly because complexes of the parent amido group often adopt stable bridging structures; and third, that when using conventional catalysts arylamines are likely more reactive than ammonia as aminating agents, so that reaction to form the diarylamine competes with formation of the aromatic primary amine. It is believed that the ligand of formula I provides an advantageous combination of stability and steric hindrance that enables the ligand to resist displacement by ammonia, and prevents bridging structures, yet induces reductive elimination from parent amido complexes, and favors reaction of ammonia with the arylating agent over that of the product arylamine.

The catalyst may be introduced into the reaction as a preformed complex comprising the ligand and the Group VIII metal. Alternatively, the catalyst may be prepared in situ in the arylation reaction mixture. If the latter approach is employed, then a Group VIII catalyst precursor compound and the ligand of formula I are independently added to the reaction mixture, wherein it is believed that a complex is formed in situ. Compounds that are suitable as precursors are Group VIII metal compounds having ligands that bind relatively weakly to the metal. Suitable precursor compounds include, for example, alkene and diene complexes of the Group VIII metals, such as di(benzylidene)acetone (dba) complexes, monodentate phosphine complexes, and Group VIII carboxylates. Alkene and diene complexes, particularly di(benzylidene)acetone (dba) complexes are preferred.

Non-limiting examples of suitable catalyst precursor compounds include [bis-di(benzylidene)acetone]palladium (0), tetrakis(triphenylphosphine)palladium (0), tris-[di(benzylidene)acetone]palladium (0), tris[di(benzylidene)acetone]dipalladium (0), palladium acetate, and the analogous complexes of iron, cobalt, nickel, ruthenium, rhodium, osmium, iridium, and platinum. Any of the aforementioned catalyst precursors may include a solvent of crystallization. Group VIII metals supported on carbon, preferably, palladium on carbon, can also be suitably employed as a precursor compound. Preferably, the catalyst precursor compound is tris-[di(benzylidene)acetone]dipalladium(0).

The quantity of catalyst which is employed in the process of this invention is any quantity which promotes the formation of the N-aryl product. Generally, the quantity is a catalytic amount, which means that the catalyst is used in an amount which is less than stoichiometric relative to the unsaturated organic sulfonate. Typically, the amount of the catalyst ranges from about 0.01 to about 20 mole percent, based on the number of moles of the Group VIII metal relative to the number of moles of the arylating compound. Preferably, the amount of the catalyst is in the range from about 0.1 to about 10 mole percent, and more preferably from about 3 to about 8 mole percent.

Generally it is believed that a 1:1 complex is formed between the Group VIII metal atom or ion and the ligand of formula I. Therefore, in general the amount of the ligand used relative to the amount of Group VIII metal is calculated to be sufficient to form a 1:1 complex. However, the ratio is not believed to be critical, since using a lesser amount will merely result in less of the active complex, while if a greater amount is used, the excess ligand will not interfere with the catalytic process. Typically it is preferable to avoid having an excess of the Group VIII metal if the source of the Group VIII metal (i.e. the catalyst precursor compound) itself may be catalytically active, so preferably the ligand is used in a stoichiometrically equivalent amount, or in excess, relative to the Group VIII metal. For the most efficient use of the transition metal and catalyst, however, it is believed that the molar ratio of the ligand of formula I to the Group VIII metal should be in the range from about 1 to about 2, preferably about 1 to about 1.5, more preferably about 1 to about 1.3.

In a particular embodiment of the invention, the catalyst may be anchored to a polymer or to a solid phase support (which may itself be a polymer). A solid phase-supported catalyst may be prepared, for example, by tethering the ligand of formula I to a polymer or solid phase support such as a polymer support. The ligand may be attached directly or by a suitable tethering group. The point of attachment may be any substitutable position of the compound of formula I. The definitions of the substituents given above should be interpreted as providing for the optional presence of such a tethering group. The person skilled in the art will know how to select suitable polymer or solid phase support, a suitable point of attachment, and a suitable tethering group. An important factor is the compatibility of the polymer, solid phase support and tethering group with the conditions of the reaction. In selecting a point of attachment to the ligand, the point of attachment will be selected so as not to interfere with the formation of the complexes involved in the process of the invention.

Although the precise mechanism of the reaction involved in the process of the invention is not known with certainty, the inventors have obtained strong evidence for the involvement in the process of the invention of a mononuclear aryl-palladium-amide complex. In particular, a schematic depiction of the catalytic cycle believed to be involved in the process of the invention in the reaction with ammonia is shown in Scheme 2 below, wherein the ligand depicted as the P—P moiety is the ligand according to formula I, M is the Group VIII metal atom or ion, and Ar—X is the arylating agent, wherein Ar represents the aromatic moiety and X represents the leaving group, and B represents the base. The reaction with lithium amide is believed to involve a similar cycle except that in the complex that is analogous to 3 the nitrogen moiety is $NH_2$ which would undergo spontaneous loss of $X^-$ without the need for the deprotonation step. In Example 31, described herein, the inventors have demonstrated an amido complex such as 4 undergoing reductive elimination reaction to form an aromatic primary amine.

Another aspect of the invention therefore relates to complexes such as those of formula 4, that are useful as intermediates in a process for the synthesis of aromatic primary amines.

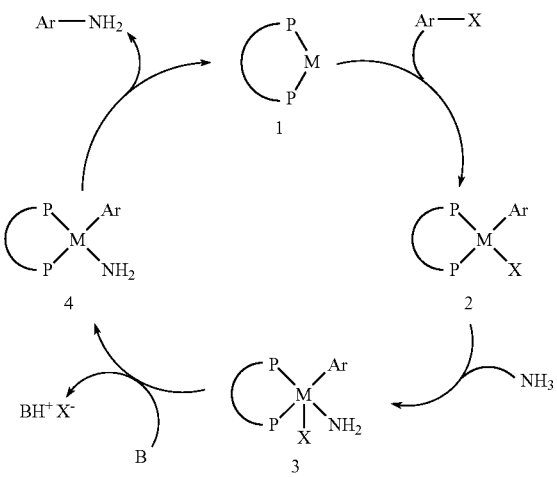

Therefore, as a further aspect of the invention, there is provided a transition metal complex according to the formula IV:

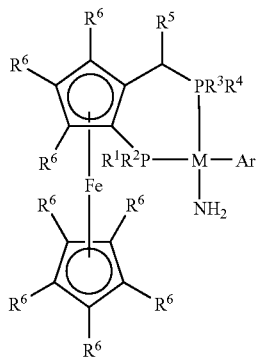

wherein:
M comprises a Group VIII metal atom or ion;
Ar represents a moiety comprising an aromatic ring wherein a carbon atom of the aromatic ring is sigma-bonded to the Group VIII metal atom or ion of M;

wherein:
$R^1$ and $R^2$ are independently selected from the group consisting of $(C_1-C_{12})$alkyl, $(C_1-C_{12})$heteroalkyl, and optionally substituted aromatic rings, or —$PR^1R^2$ is a radical of the formula II:

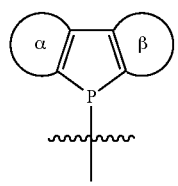

wherein α and β are optionally substituted aromatic rings;
$R^3$ and $R^4$ are independently selected from the group consisting of $(C_1-C_{12})$alkyl, $(C_1-C_{12})$heteroalkyl, and optionally substituted aromatic rings, or —$PR^3R^4$ is a radical of the formula II;
$R^5$ is selected from the group consisting of hydrogen, $(C_1-C_8)$alkyl, $(C_1-C_8)$heteroalkyl and optionally substituted aromatic rings,
each $R^6$ is independently selected from the group consisting of hydrogen, and $(C_1-C_4)$alkyl;
wherein each of said optionally substituted aromatic rings is either unsubstituted or substituted at any substitutable position with one or more substituents independently selected from the group consisting of $(C_1-C_4)$alkyl, $(C_1-C_4)$heteroalkyl, $(C_1-C_3)$ fluorinated alkyl, —$OR^7$, —$SR^7$, and $NR^7_2$;
each $R^7$ is independently selected from the group consisting of $(C_1-C_4)$alkyl and $(C_1-C_4)$heteroalkyl, or, within any occurrence of $NR^7_2$, independently of any other occurrence of $NR^7_2$ the two $R^7$ groups in combination form $(C_4-C_8)$alkylene or $(C_4-C_8)$heteroalkylene;
or any one occurrence of $R^6$, or any one substitutable position of any one of the groups $R^1$, $R^2$, $R^3$, $R^4$, $R^5$ and $R^7$, is a point of attachment, directly or via a tethering group, to a polymer or a solid phase support.

In the complex of formula IV, M comprises a Group VIII metal or ion. The Group VIII metal atom or ion is coordinated by the two phosphorus atoms of the ligand of formula I, and the —Ar and —$NH_2$ groups. When it is said that the M "comprises" the Group VIII metal atom or ion, it is envisaged that the metal atom or ion may optionally be coordinated by further ligands, depending on the precise nature of the Group VIII metal involved, and the presence or otherwise of potentially coordinating ligands in the medium in which the complex of formula IV is contained. In preferred embodiments of complexes of formula IV, the Group VIII metal is palladium.

The particular and preferred embodiments of the complexes of formula IV, including those wherein the Group VIII metal is palladium, are those where the complex of formula IV is an embodiment of the ligand of formula I that is used in the particular and preferred embodiments of the process of the invention. Those embodiments of the ligand of formula I that are preferred in the process of the invention are also preferred in the complex of formula IV.

In a preferred embodiment, of this aspect of the invention, the complex is a complex of formula IVa:

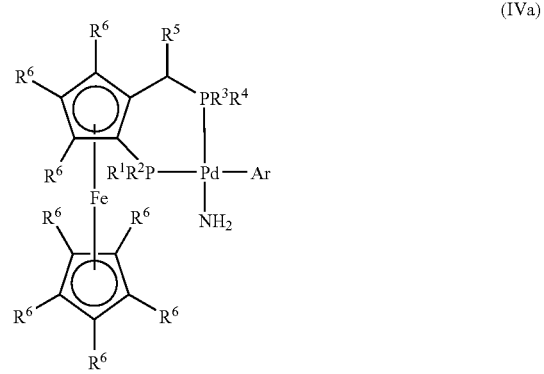

wherein:
$R^1$, $R^2$, $R^3$, $R^4$, $R^5$, and $R^6$, are as defined above for formula IV; and
the palladium is optionally by coordinated by up to two additional ligands.

Particular and preferred embodiments of the complex of formula IVa are those comprising an embodiment of the ligand of formula I used in a particular or preferred embodiment of the process of the invention.

Preferred embodiments of the complex of formula IVa include those wherein $R^3$ and $R^4$ are each t-butyl, $R^5$ is hydrogen or methyl, preferably methyl, and each $R^6$ is hydrogen.

Another aspect of the invention relates to compositions that are useful as reagents for the synthesis of aromatic primary amines. In this aspect of the invention, a composition is provided, the composition comprising:
(a) an ammoniating agent selected from the group consisting of:
(i) ammonia; and
(ii) a metal amide; and
(b) a complex comprising:
(i) a Group VIII metal atom or ion; and
(ii) a ligand, wherein the ligand is a compound of formula I:

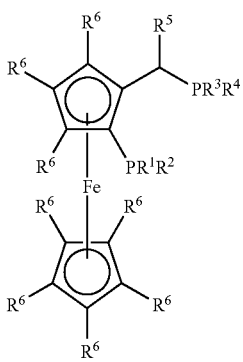

(I)

wherein:
R¹ and R² are independently selected from the group consisting of $(C_1$-$C_{12})$alkyl, $(C_1$-$C_{12})$heteroalkyl, and optionally substituted aromatic rings, or —PR¹R² is a radical of the formula II:

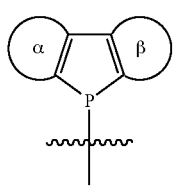

(II)

wherein α and β are optionally substituted aromatic rings;
R³ and R⁴ are independently selected from the group consisting of $(C_1$-$C_{12})$alkyl, $(C_1$-$C_{12})$heteroalkyl, and optionally substituted aromatic rings, or —PR³R⁴ is a radical of the formula II;
R⁵ is selected from the group consisting of hydrogen, $(C_1$-$C_8)$alkyl, $(C_1$-$C_8)$heteroalkyl and optionally substituted aromatic rings,
each R⁶ is independently selected from the group consisting of hydrogen, and $(C_1$-$C_4)$alkyl;
wherein each of said optionally substituted aromatic rings is either unsubstituted or substituted at any substitutable position with one or more substituents independently selected from the group consisting of $(C_1$-$C_4)$alkyl, $(C_1$-$C_4)$heteroalkyl, $(C_1$-$C_3)$ fluorinated alkyl, —OR⁷, —SR⁷, and NR⁷₂;
each R⁷ is independently selected from the group consisting of $(C_1$-$C_4)$alkyl and $(C_1$-$C_4)$heteroalkyl, or, within any occurrence of NR⁷₂, independently of any other occurrence of NR⁷₂ the two R⁷ groups in combination form $(C_4$-$C_8)$alkylene or $(C_4$-$C_8)$heteroalkylene;
or any one occurrence of R⁶, or any one substitutable position of any one of the groups R¹, R², R³, R⁴, R⁵ and R⁷, is a point of attachment, directly or via a tethering group, to a polymer or a solid phase support;
provided that when the ammoniating agent is ammonia, the composition further comprises a base.

The particular and preferred embodiments of this aspect of the invention are those which are used in the particular and preferred embodiments of the process of the invention herein described. Preferred compositions of the invention are include those wherein the Group VIII metal is palladium and those comprising a ligand that is a preferred embodiment of the ligands of formula I for use in the process of the invention herein described.

The process described herein may be conducted in any conventional reactor designed for catalytic processes. Continuous, semi-continuous, and batch reactors can be employed. If the catalyst is substantially dissolved in the reaction mixture as in homogeneous processes, then batch reactors, including stirred tank and pressurized autoclaves, can be employed. If the catalyst is anchored to a support and is substantially in a heterogeneous phase, then fixed-bed and fluidized bed reactors can be used. In the typical practice of this invention, the arylating agent, ammoniating agent, and catalyst are mixed in a batch, preferably with a solvent, and the resulting mixture is maintained at a temperature and pressure effective to prepare the aromatic primary amine product. When the ammoniating agent comprises ammonia, it may be desirable to perform the reaction under an atmosphere comprising ammonia gas and/or under elevated pressure. A reaction vessel that is suitable for performing reactions at elevated pressure will be desirable for performing the process of the invention under such conditions.

Any solvent can be used in the process of the invention, provided that it does not react under the conditions of the process such as to interfere with the formation of the aromatic primary amine product. Both aprotic and protic solvents and combinations thereof are acceptable. Suitable aprotic solvents include, but are not limited to, aromatic hydrocarbons, such as toluene and xylene, chlorinated aromatic hydrocarbons, such as dichlorobenzene, and ethers, such as 1,2-dimethoxyethane, tetrahydrofuran, 1,4-dioxane, t-butylmethyl ether. Suitable protic solvents include, but are not limited to, water and aliphatic alcohols, such as ethanol, isopropanol, and cyclohexonol, as well as glycols and other polyols. The preferred solvents are aromatic hydrocarbon solvents such as toluene and xylene and ether solvents such as 1,2-dimethoxyethane and tetrahydrofuran. The preferred solvent is 1,2-dimethoxyethane. The amount of solvent which is employed may be any amount, preferably an amount sufficient to at least partially solubilize all the reactants. A suitable quantity of solvent typically ranges from about 1 to about 100 grams solvent per gram reactants. Other quantities of solvent may also be suitable, as determined by the specific process conditions and by the skilled artisan.

Generally, the reagents may be mixed together or added to a solvent in any order. The reaction is preferably performed in the absence of oxygen, although rigorous exclusion of oxygen is not always necessary. If it is desirable or necessary to remove air, the solvent and reaction mixture can be sparged with a non-reactive gas, such as nitrogen, helium, or argon, or the reaction may be conducted under anaerobic conditions. The process conditions can be any operable conditions which yield the desired aromatic primary amine product. Beneficially, the reaction conditions for this process are mild. For example, a preferred temperature for the process of the present invention ranges from about ambient temperature, taken as about 10° C., to about 150° C., preferably, from about 80° C. to about 110° C. The process is generally run for a time sufficient to convert as much as possible of the arylating agent to the aromatic primary amine. Typical reaction times range from about 30 minutes to about 24 hours, but longer times may be used if necessary.

In some embodiments of the process of the invention, the aromatic primary amine is isolated from the reaction mixture. The aromatic primary amine product can be isolated by conventional methods known to those skilled in the art, including, for example, distillation, crystallization, sublimation, and gel chromatography. The yield of product will vary depending upon the specific catalyst, reagents, and process conditions used. "Yield" is defined as the mole percentage of aromatic primary amine product recovered, based on the number of moles of the arylating agent employed. Typically, the yield of the aromatic primary amine product is greater than about 25%. In preferred embodiments of the invention, the yield of the aromatic primary amine product is greater than about 60%, and more preferably, is greater than about 80%.

In other embodiments of the invention, the amine may be converted to another useful product by reaction without the intermediate isolation of the primary amine.

EXAMPLES

The following non-limiting examples are provided to illustrate the invention. The methods are applicable to other embodiments of the invention. Although the examples provided are believed to be typically effective to perform the process of the invention, the person skilled in the art will appreciate that, due to variations in the reactivity of different arylating agents, ammoniating agents, and catalysts it may be necessary to vary the procedures for any given embodiment of the invention. For example, reaction monitoring, such as by using thin layer chromatography or HPLC, may be used to determine the optimum reaction time. Products may be purified by conventional techniques that will vary, for example, according to the amount of side products produced and the physical properties of the compounds. On a laboratory scale, recrystallisation from a suitable solvent, column chromatography, normal or reverse phase HPLC, or distillation are all techniques which may be useful. The person skilled in the art will appreciate how to vary the reaction conditions to synthesize any given compound within the scope of the invention without undue experimentation. See, e.g., *Vogel's Textbook of Practical Organic Chemistry*, by A. I. Vogel, et al., *Experimental Organic Chemistry: Standard and Microscale*, by L. M. Harwood et al. (2nd Ed., Blackwell Scientific Publications, 1998), and Advanced Practical Organic Chemistry, by J. Leonard, et al. (2nd Edition, CRC Press 1994). Further discussion of the results described herein is provided by the inventors in Q. Shen and J. F. Hartwig, *J. Am. Chem. Soc.*, 2006, 128, 10028-29 and the supporting information thereto.

General Methods

Unless otherwise noted, all manipulations were conducted under an inert atmosphere. $^1$H and $^{13}$C NMR spectra were recorded on a Bruker DPX 400 or 500 MHz Spectrometer, and $^{31}$P {$^1$H} NMR spectra were recorded on a General Electric QE 300 MHz spectrometer with tetramethylsilane or residual protiated solvent as a reference. All $^{31}$P {$^1$H} NMR chemical shifts are reported in parts per million relative to an 85% $H_3PO_4$ external standard. Chemical shifts downfield of the standard are reported as positive values. Elemental analyses were performed by Atlantic Microlabs Inc., Norcross, Ga. or Robertson Microlab, Inc., Madison, N.J. GC and GC/MS analyses were conducted with an HP-1 methyl silicone column. 1-dicyclohexylphosphino-2-di-t-butylphosphinoethyl-ferrocene ("CyPF-t-Bu") and $Pd(CH_3CN)_2Cl_2$ were obtained from Solvias AG and Strem Chemicals and used without further purification. 1,2-Dimethoxyethane (DME, 99.9% purity, HPLC grade) was purchased and used without further purification. All other chemicals were used as received from commercial sources.

Example 1

Synthesis of (CyPF-t-Bu)PdCl$_2$

CyPF-t-Bu (55.4 mg 0.100 mmol) was added to a solution of $Pd(CH_3CN)_2Cl_2$ (26.0 mg, 0.100 mmol) in $CH_2Cl_2$ (5.0 mL). The resulting mixture was stirred for 30 min. at room temperature. The reaction mixture was filtered through a medium fritted funnel containing diatomaceous earth ("Celite®"). The resulting solution was concentrated under vacuum. Crystalline material was obtained by layering with hexane and cooling at −10° C. (65.0 mg, 90%). $^1$H NMR (CDCl$_3$) δ 4.85 (s, 1 H), 4.55 (s, 1 H), 4.53 (s, 1 H), 4.25 (s, 5 H), 3.60-3.75 (m, 1 H), 3.00-3.10 (m, 1 H), 2.50-2.60 (m, 1 H), 2.27-2.90 (m, 1 H), 2.13-2.25 (m, 2 H), 2.00-2.10 (m, 1 H), 1.97 (dd, J=9.0, 7.5 Hz, 3 H), 1.70-1.95 (m, 4 H), 1.20-1.30 (m, 8 H), 1.63 (d, J=13.0 Hz, 9 H), 1.30-1.45 (m, 4 H), 1.23 (d, J=14.5 Hz, 9 H); $^{31}$P {$^1$H} NMR (CH$_2$Cl$_2$) δ 113.83 (d, J=9.7 Hz), 31.78 (d, J=9.7 Hz); $^{13}$C NMR (CDCl$_3$) δ 96.49 (dd, J=13.3, 5.5 Hz), 71.92 (d, J=2.5 Hz), 69.90 (d, J=9.1 Hz), 69.78, 69.63 (d, J=9.2 Hz), 69.34 (t, J=5.7 Hz), 41.6 (d, J=35.5 Hz), 41.57 (d, J=8.2 Hz), 40.55 (d, J=11.2 Hz), 37.56 (d, J=35.5 Hz), 34.48 (t, J=9.1 Hz), 31.97 (d, J=1.9 Hz), 31.05 (d, J=1.9 Hz), 29.99, 29.19, 28.06, 27.55 (d, J=6.8 Hz), 27.32 (d, J=10.2 Hz), 26.98 (d, J=12.6 Hz), 26.89 (d, J=5.2 Hz), 26.78 (d, J=3.8 Hz), 26.12 (d, J=1.9 Hz), 25.55, 18.02 (d, J=6.7 Hz). Anal. Calcd. For $C_{32}H_{52}Cl_2FeP_2Pd$: C, 52.51; H, 7.16. Found: C, 52.72; H, 7.38.

Catalytic Amination of Aromatic Chlorides, Bromides and Iodides with Ammonia. (Examples 2-10).

Table 1 lists the results of experiments in which various arylating agents were treated with ammonia in 1,2-dimethoxyethane in the presence of (CyPF-t-Bu)PdCl$_2$ (1.0 mol %) and sodium t-butoxide as the base. The conditions for each experiment are indicated in Table 1. A procedure typical of those used is described in Example 1 for the conditions used in Entry 1 of Table 1. The conditions used for the other experiments (described as Examples 2-10) were analogous to those described for Example 1. In the Scheme in Table 1, Ar—X represents the arylating agent, wherein Ar represents the aromatic group and X represents the leaving group.

TABLE 1

Coupling of Aryl halides with ammonia catalyzed by CyPF-t-BuPdCl$_2$.[a]

$$\text{Ar—X} + \text{NH}_3 \xrightarrow[\text{DME}]{\underset{\text{NaOtBu}}{\text{CyPF-t-BuPdCl}_2}} \underset{\text{A}}{\text{Ar—NH}_2} + \underset{\text{B}}{\text{Ar}_2\text{NH}}$$

| Entry | Ex. | Arylating agent | Conc. | Conditions | Product | Yield[b] (%) | Ratio[c] (A/B) |
|---|---|---|---|---|---|---|---|
| 1 | 2 | 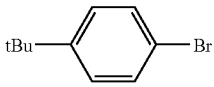 | 0.05M | 90° C., 24 h | 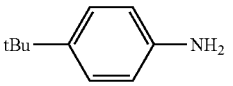 | 86 | 17:1 |

TABLE 1-continued

Coupling of Aryl halides with ammonia catalyzed by CyPF-t-BuPdCl$_2$.[a]

$$Ar-X + NH_3 \xrightarrow[\text{DME}]{\text{CyPF-t-BuPdCl}_2, \text{NaOtBu}} \underset{A}{Ar-NH_2} + \underset{B}{Ar_2NH}$$

| Entry | Ex. | Arylating agent | Conc. | Conditions | Product | Yield[b] (%) | Ratio[c] (A/B) |
|---|---|---|---|---|---|---|---|
| 2 | — | tBu-C$_6$H$_4$-OTf | 0.05M | 90° C., 24 h | —[d] | — | — |
| 3 | 3 | 2-chlorotoluene | 0.05M | 90° C., 24 h | 2-methylaniline | 69 | 23:1 |
| 4 | 4 | 2-bromotoluene | 0.05M | 90° C., 24 h | 2-methylaniline | 86 | >50:1 |
| 5 | 5 | 2-iodotoluene | 0.05M | 90° C., 24 h | 2-methylaniline | 79 | >50:1 |
| 6 | 6 | 2-bromobiphenyl | 0.05M | 90° C., 24 h | 2-aminobiphenyl | 94 | 31:1 |
| 7 | 7 | 2-bromo-iPr-benzene | 0.25M | 90° C., 20 h | 2-iPr-aniline | 89 | >50:1 |
| 8 | 8 | 4-bromoisoquinoline | 0.05M | 90° C., 20 h | 4-aminoisoquinoline | 80 | >50:1 |
| 9 | 9 | 5-bromoisoquinoline | 0.25M | 90° C., 20 h | 5-aminoisoquinoline | 70 | >50:1 |
| 10 | 10 | 1-bromonaphthalene | 0.25M | 90° C., 20 h | 1-bromonaphthalene | 92 | >50:1 |

[a]Reactions conducted in a Parr bomb with 1.0 mol % of Pd(CyPF-t-Bu)Cl$_2$, 1 mmol of ArBr, 2.0 equiv of NaOtBu at 90° C. in DME (20.0 mL)
[b]Isolated Yield;
[c]Determined by $^1$H NMR of the crude product;
[d]No aniline product, only the phenol was observed.

Example 2

4-t-Butylaniline (Table 1, Entry 1)

(CyPF-t-Bu)PdCl$_2$ (7.30 mg, 1.00×10$^{-2}$ mmol), NaOtBu (0.192 g, 2.00 mmol) and 4-t-butyl-1-bromobenzene (0.213 g, 1.00 mmol) were weighed into a Parr Bomb inside a dry box. DME (20.0 mL) was then added. The Parr bomb was closed and removed from the dry box. Ammonia was added with stirring by connecting to an ammonia tank and maintaining the pressure at 80 psi for 30 min. The resulting reaction mixture was allowed to stir for 24 h at 90° C. Pressure was built up to 200 psi during the reaction. The reaction mixture was then cooled to room temperature before being poured into ice water (20.0 mL). To this mixture was added HCl aqueous solution (10.0 mL, 1.0 M)). The mixture was stirred at room temperature for 5 min and was then neutralized with a saturated solution of NaHCO$_3$ (5.00-10.0 mL). After extraction with CH$_2$Cl$_2$ (3×20.0 mL), the organic layer was separated and dried over MgSO$_4$. The solvent was evaporated, and the crude product isolated by eluting with hexane/ethyl acetate (70/30) to give 128.1 mg (86%) of 4-t-butylaniline as a pale yellow liquid. $^1$H NMR (CDCl$_3$) δ 7.05 (d, J=8.4 Hz, 2 H), 6.55 (d, J=8.8 Hz, 2 H), 3.44 (s, br, 2 H), 1.20 (s, 9 H); $^{13}$C NMR (CDCl$_3$) δ 143.74, 141.32, 125.98, 114.86, 33.85, 31.49.

Example 3 o-Toluidine (Table 1, Entry 3)

2-Chlorotoluene (0.126 g, 1.00 mmol), (CyPF-t-Bu)PdCl$_2$ (7.30 mg, 1.00×10$^{-2}$ mmol), and NaOtBu (0.192 g, 2.00 mmol) in 20.0 mL DME gave 73.6 mg (69%) of o-toluidine as a colorless liquid (hexane/ethyl acetate: 70/30). $^1$H NMR (CDCl$_3$) δ 7.08 (d, J=6.4 Hz, 1 H), 7.07 (t, J=6.4 Hz, 1 H), 6.74 (t, J=6.0 Hz, 1 H), 6.70 (d, J=6.0 Hz, 1 H), 3.62 (s, br, 2 H), 2.19 (s, 3 H); $^{13}$C NMR (CDCl$_3$) δ 144.41, 130.36, 126.87, 122.26, 118.57, 114.88, 17.25.

Example 4 o-Toluidine (Table 1, Entry 4)

2-Bromotoluene (0.171 g, 1.00 mmol), (CyPF-t-Bu)PdCl$_2$ (7.30 mg, 1.00×10$^{-2}$ mmol), and NaOtBu (0.192 g, 2.00 mmol) in 20.0 mL DME gave 89.1 mg (86%) of o-toluidine as a colorless liquid.

Example 5 o-Toluidine (Table 1, Entry 5)

2-Iodotoluene (0.217 g, 1.00 mmol), (CyPF-t-Bu)PdCl$_2$ (7.30 mg, 1.00×10$^{-2}$ mmol), and NaOtBu (0.192 g, 2.00 mmol) in 20.0 mL DME gave 84.7 mg (79%) of o-toluidine as a colorless liquid.

Example 6

2-Aminobiphenyl (Table 1, Entry 6)

2-Bromobiphenyl (0.233 g, 1.00 mmol), (CyPF-t-Bu)PdCl$_2$ (7.30 mg, 1.00×10$^{-2}$ mmol), and NaOtBu (0.192 g, 2.00 mmol) in 20.0 mL DME gave 0.160 g (94%) of 2-aminobiphenyl as a solid (hexane/ethyl acetate: 70/30). $^1$H NMR (CDCl$_3$) δ 7.28-7.34 (m, 4 H), 7.19-7.25 (m, 1 H), 6.98-7.07 (m, 2 H), 6.71 (t, J=7.2 Hz, 1 H), 6.62 (d, J=8.0 Hz, 1 H), 3.60 (s, br, 2 H); $^{13}$C NMR (CDCl$_3$) δ 140.40, 139.44, 130.36, 129.00, 128.71, 128.41, 127.52, 127.06, 118.54, 115.50.

Example 7

2-i-Propylaniline (Table 1, Entry 7)

1-Bromo-2-i-propylbenzene (0.199 g, 1.00 mmol), (CyPF-t-Bu)PdCl$_2$ (7.30 mg, 1.00×10$^{-2}$ mmol), and NaOtBu (0.192 g, 2.00 mmol) in 4.0 mL DME gave 0.120 g (89%) of 2-i-propylaniline as a solid (hexane/ethyl acetate: 70/30).
$^1$H NMR (CDCl$_3$) δ 7.08 (dd, J=6.0, 1.2 Hz, 1 H), 6.96 (td, J=6.0, 1.2 Hz, 1 H), 6.73 (td, J=6.0, 0.8 Hz, 1 H), 6.60 (dd, J=6.0, 1.2 Hz, 1 H), 3.56 (s, br, 2 H), 2.83 (sept, J=5.2 Hz, 1 H), 1.20 (J=5.2 Hz, 6 H); $^{13}$C NMR (CDCl$_3$) δ 143.22, 132.55, 126.44, 125.30, 118.92, 115.74, 27.56, 22.20.

Example 8

4-Amino-iso-quinoline (Table 1, Entry 8)

4-Bromo-iso-quinoline (0.208 g, 1.00 mmol), (CyPF-t-Bu)PdCl$_2$ (7.30 mg, 1.00×10$^{-2}$ mmol), and NaOtBu (0.192 g, 2.00 mmol) in 20.0 mL DME gave 0.115 g (80%) of 4-amino-iso-quinoline as a solid Ethyl acetate/methanol:50/50).
$^1$H NMR (CDCl$_3$) δ 8.70 (s, 1 H), 8.00 (s, 1 H), 7.84 (d, J=8.0 Hz, 1 H), 7.76 (d, J=8.5 Hz, 1 H), 7.58 (dd, J=8.0, 7.0 Hz, 1 H), 7.51 (dd, J=8.0, 7.5 Hz, 1 H), 4.21 (s, 2 H); $^{13}$C NMR (CDCl$_3$) δ 142.99, 136.86, 128.86, 128.54, 127.99, 127.65, 126.93, 125.95, 119.97.

Example 9

5-Amino-iso-quinoline (Table 1, Entry 9)

5-Bromo-iso-quinoline (0.208 g, 1.00 mmol), (CyPF-t-Bu)PdCl$_2$ (7.30 mg, 1.00×10$^{-2}$ mmol), and NaOtBu (0.192 g, 2.00 mmol) in 4.0 mL DME gave 0.101 g (70%) of 5-Amino-iso-quinoline as a solid (Ethyl acetate/methanol:90/10). $^1$H NMR (CDCl$_3$) δ 9.15 (s, 1 H), 8.45 (d, J=5.6 Hz, 1 H), 7.55 (d, J=6.0 Hz, 1 H), 7.37 (d, J=5.2 Hz, 2 H), 6.91 (t, J=4.8 Hz, 1 H), 4.26 (s, br, 2 H); $^{13}$C NMR (CDCl$_3$) δ 152.85, 141.88, 141.30, 129.33, 127.72, 125.88, 117.80, 114.06, 112.96.

Example 10

1-Aminonaphthalene (Table 1, Entry 10)

1-Bromonapthathene (0.207 g, 1.00 mmol), (CyPF-t-Bu)PdCl$_2$ (7.30 mg, 1.00×10$^{-2}$ mmol), and NaOtBu (0.192 g, 2.00 mmol) in 4.0 mL DME gave 0.132 g (92%) of 1-Aminonaphthalene as a solid (hexane/ethyl acetate: 70/30). $^1$H NMR (CDCl$_3$) δ 7.78-7.82 (m, 2 H), 7.40-7.7.47 (m, 2 H), 7.25-7.34 (m, 2 H), 6.76 (dd, J=6.8, 1.2 Hz, 1 H), 4.10 (s, br, 2 H); $^{13}$C NMR (CDCl$_3$) δ 140.02, 134.32, 128.49, 126.29, 125.79, 124.80, 123.58, 120.74, 118.90, 109.62.

Catalytic Amination of Heteroaryl and Aryl Chlorides, Bromides and Iodides with Lithium Amide (LiNH$_2$). (Examples 11-23).

Table 2 lists the results of experiments in which various arylating agents were treated with LiNH$_2$ in DME in the presence of (CyPF-t-Bu)PdCl$_2$ (1.0 mol %). The conditions for each experiment are indicated in Table 2. The monoarylation:diarylation selectivities for reactions of lithium amide were slightly lower than those of reactions with ammonia (c.f. Table 1), but were acceptable. A procedure typical of those used is described in Example 11 for the conditions used in Entry 1 of Table 2. The procedures used for the other experiments (Examples 12-16 and 18-23) were analogous to those of Example 11. For the reaction of 1-bromo-2-i-propylbenzene, the amination reaction was also performed on a large scale [1.99 g (10 mmol) of the starting material] as described in Example 17. In the Scheme in Table 2, Ar—X represents the arylating agent, wherein Ar represents the aromatic group and X represents the leaving group.

TABLE 2

Coupling of Aryl Halides with LiNH$_2$ Catalyzed by CyPF-t-BuPdCl$_2$.[a]

$$Ar-X + LiNH_2 \xrightarrow[DME]{CyPF\text{-}t\text{-}BuPdCl_2} \underset{A}{Ar-NH_2} + \underset{B}{Ar_2NH}$$

| Entry | Ex. | Arylating agent | Conc. | Conditions | Product | Yield (%)[b] | Ratio[c] (A/B) |
|---|---|---|---|---|---|---|---|
| 1 | 11 | tBu—C$_6$H$_4$—Br | 0.05M | 80° C., 24 h | tBu—C$_6$H$_4$—NH$_2$ | 72 | 9.5:1 |
| 2 | — | tBu—C$_6$H$_4$—OTf | 0.05M | 80° C., 24 h | —[d] | — | — |
| 3 | — | tBu—C$_6$H$_4$—OTs | 0.05M | 80° C., 24 h | —[d] | — | — |
| 4 | 12 | 2-methyl-chlorobenzene | 0.05M | 80° C., 24 h | 2-methyl-aniline | 75 | 11.1:1 |
| 5 | 13 | 2-methyl-bromobenzene | 0.05M | 80° C., 24 h | 2-methyl-aniline | 86 | >50:1 |
| 6 | 14 | 2-methyl-iodobenzene | 0.05M | 80° C., 24 h | 2-methyl-aniline | 81 | >50:1 |
| 7 | 15 | 2-bromobiphenyl | 0.05M | 80° C., 24 h | 2-aminobiphenyl | 76 | 12:1 |
| 8 | 16 | 1-bromo-2-iPr-benzene | 0.25M | 90° C., 24 h | 2-iPr-aniline | 81 | >50:1 |
|   | 17 |   |   |   |   | 82[e] | >50:1 |
| 9 | 18 | 4-bromoisoquinoline | 0.05M | 80° C., 20 h | 4-aminoisoquinoline | 82 | >50:1 |
| 10 | 19 | 5-bromoisoquinoline | 0.5M | 90° C., 24 h | 5-aminoisoquinoline | 79 | >50:1 |

TABLE 2-continued

Coupling of Aryl Halides with LiNH$_2$ Catalyzed by CyPF-t-BuPdCl$_2$.[a]

$$Ar-X + LiNH_2 \xrightarrow[DME]{CyPF\text{-}t\text{-}BuPdCl_2} \underset{A}{Ar-NH_2} + \underset{B}{Ar_2NH}$$

| Entry | Ex. | Arylating agent | Conc. | Conditions | Product | Yield (%)[b] | Ratio[c] (A/B) |
|---|---|---|---|---|---|---|---|
| 11 | 20 | 1-bromonaphthalene | 0.25M | 80° C., 20 h | 1-aminonaphthalene (Br shown) | 89 | >50:1 |
| 12 | 21 | 2-bromonaphthalene | 0.25M | 80° C., 20 h | 2-aminonaphthalene | 69 | 8.0:1 |
| 13 | 22 | 1-chloro-4-bromobenzene | 0.5M | 60° C., 20 h | 4-chloroaniline | 68 | 10.9:1 |
| 14 | 23 | 2,2'-dibromobiphenyl | 0.5M | 90° C., 24 h | carbazole | 64 | — |

[a]Reactions conducted with 1.0 mol % of Pd(CyPF-t-Bu)Cl$_2$, 1 mmol ArBr, 10 equiv LiNH$_2$ in 20 mL DME.
[b]Isolated Yield;
[c]Determined by $^1$H NMR of the crude product;
[d]No product, only the phenol was detected.
[e]Reaction with 1.99 g of 1-bromo-2-i-propylbenzene (10 mmol).

Example 11

4-t-Butylaniline (Table 2, Entry 1)

(CyPF-t-Bu)PdCl$_2$ (7.30 mg, 1.00×10$^{-2}$ mmol), LiNH$_2$ (0.230 g, 10.0 mmol) and 4-t-butyl-1-bromobenzene (0.213 g, 1.00 mmol) were weighed into a 24 mL vial. DME (20.0 mL) was then added. The vial was sealed with a cap containing a PTFE septum, and the reaction mixture was stirred for 24 h at 80° C. The reaction mixture was allowed to cool to room temperature before pouring into ice water (20.0 mL). To this mixture was added HCl aqueous solution (10.0 mL, 1.0 M). The mixture was stirred at room temperature for 5 min and was then neutralized with a saturated solution of NaHCO$_3$ (5.00-10.0 mL). After extraction with CH$_2$Cl$_2$ (3×20.0 mL), the organic layer was separated and dried over MgSO$_4$. The solvent was evaporated, and the crude product isolated by eluting with hexane/ethyl acetate (80/20) to give 107.0 mg (72%) of 4-t-butylaniline as a pale yellow liquid.

Example 12 o-Toluidine (Table 2, Entry 4)

2-Chlorotoluene (0.126 g, 1.00 mmol), (CyPF-t-Bu)PdCl$_2$ (7.30 mg, 1.00×10$^{-2}$ mmol), and LiNH$_2$ (0.230 g, 10.0 mmol) in 20.0 mL DME gave 74.9 mg (70%) of o-toluidine as a colorless liquid.

Example 13 o-Toluidine (Table 2, Entry 5)

2-Bromotoluene (0.171 g, 1.00 mmol), (CyPF-t-Bu)PdCl$_2$ (7.30 mg, 1.00×10$^{-2}$ mmol), and LiNH$_2$ (0.230 g, 10.0 mmol) in 20.0 mL DME gave 89.5 mg (86%) of o-toluidine as a colorless liquid.

Example 14 o-Toluidine (Table 2, Entry 6)

2-Iodotoluene (0.217 g, 1.00 mmol), (CyPF-t-Bu)PdCl$_2$ (7.30 mg, 1.00×10$^{-2}$ mmol), and LiNH$_2$ (0.230 g, 10.0 mmol) in 20.0 mL DME gave 86.8 mg (81%) of o-toluidine as a colorless liquid.

Example 15

2-Aminobiphenyl (Table 2, Entry 7)

2-Bromobiphenyl (0.233 g, 1.00 mmol), (CyPF-t-Bu)PdCl$_2$ (7.30 mg, 1.00×10$^{-2}$ mmol), and LiNH$_2$ (0.230 g, 10.0 mmol) in 20.0 mL DME gave 0.129 g (76%) of 2-Aminobiphenyl as a solid.

Example 16

2-i-Propylaniline (Table 2, Entry 8)

1-Bromo-2-i-propylbenzene (0.199 g, 1.00 mmol), (CyPF-t-Bu)PdCl$_2$ (7.30 mg, 1.00×10$^{-2}$ mmol), and LiNH$_2$ (0.230 g, 10.0 mmol) in 2.0 mL DME gave 0.109 g (81%) of 2-i-Propylaniline as a solid.

Example 17 i-Propylaniline. Procedure for Large-Scale Catalytic Amination of 1-Bromo-2-i-propyl Benzene with Lithium Amide (Table 2, Entry 8)

(CyPF-t-Bu)PdCl$_2$ (73.0 mg, 100 mmol), LiNH$_2$ (2.30 g, 100 mmol) and 1-Bromo-2-i-propylbenzene (1.99 g, 100 mmol) were weighed into a 100 mL round bottom flask with a stirring bar. DME (20.0 mL) was then added. The flask was sealed with a cap and wrapped tightly with electrical tape. The reaction mixture was stirred for 24 h at 90° C. The reaction mixture was allowed to cool to room temperature before pouring into ice water (50.0 mL). To this mixture was added aqueous HCl (100 mL, 1.0 M). The mixture was stirred at room temperature for 5 min and was then neutralized with a saturated solution of NaHCO$_3$ (50.0 mL). After extraction with CH$_2$Cl$_2$ (3×50.0 mL), the organic layer was separated and dried over MgSO$_4$. The solvent was evaporated, and the crude product isolated by column chromatography, eluting with hexane/ethyl acetate (70/30) to give 1.11 g (82%) of 2-i-propylaniline as a solid.

Example 18

4-Amino-iso-quinoline (Table 2, Entry 9)

4-Bromo-iso-quinoline (0.208 g, 1.00 mmol), (CyPF-t-Bu)PdCl$_2$ (7.30 mg, 1.00×10$^{-2}$ mmol), and LiNH$_2$ (0.230 g, 10.0 mmol) in 20.0 mL DME gave 0.118 g (82%) of 4-Amino-iso-quinoline as a solid.

Example 19

5-Amino-iso-quinoline (Table 2, Entry 10)

5-Bromo-iso-quinoline (0.208 g, 1.00 mmol), (CyPF-t-Bu)PdCl$_2$ (7.30 mg, 1.00×10$^{-2}$ mmol), and LiNH$_2$ (0.230 g, 10.0 mmol) in 2.0 mL DME gave 0.114 g (79%) of 5-Amino-iso-quinoline as a solid.

Example 20

1-Aminonaphthalene (Table 2, Entry 11)

1-Bromonapthathene (0.207 g, 1.00 mmol), (CyPF-t-Bu)PdCl$_2$ (7.30 mg, 1.00×10$^{-2}$ mmol), and LiNH$_2$ (0.230 g, 10.0 mmol) in 4.0 mL DME gave 0.128 g (89%) of 1-Aminonaphthalene as a solid.

Example 21

2-Aminonaphthalene (Table 2, Entry 12)

2-Bromonapthathene (0.207 g, 1.00 mmol), (CyPF-t-Bu)PdCl$_2$ (7.30 mg, 1.00×10$^{-2}$ mmol), and LiNH$_2$ (0.230 g, 10.0 mmol) in 4.0 mL DME gave 0.100 g (69%) of 1-Aminonaphthalene as a solid (hexane/ethyl acetate: 70/30). $^1$H NMR (CDCl$_3$) δ 7.67 (d, J=8.4 Hz, 1 H), 7.63 (d, J=8.4 Hz, 1 H), 7.57 (d, J=8.0 Hz, 1 H), 7.35 (td, J=7.2, 1.2 Hz, 1 H), 7.21 (td, J=7.2, 1.6 Hz, 1 H), 6.93 (s, 1 H), 6.90 (dd, J=8.4, 2.0 Hz, 1 H), 3.76 (s, br, 2 H); $^{13}$C NMR (CDCl$_3$) δ 144.05, 134.83, 129.12, 127.86, 127.65, 126.27, 125.73, 122.38, 118.17, 108.48.

Example 22

1-Amino-4-chlorobenzene (Table 2, Entry 13)

1-Bromo-4-chlorobenzene (0.207 g, 1.00 mmol), (CyPF-t-Bu)PdCl$_2$ (7.30 mg, 1.00×10$^{-2}$ mmol), and LiNH$_2$ (0.230 g, 10.0 mmol) in 2.0 mL DME gave 86.7 mg (68%) of 1-Amino-4-chlorobenzene as a solid (hexane/ethyl acetate: 70/30). $^1$H NMR (CDCl$_3$) δ 7.08 (d, J=8.4 Hz, 2 H), 6.58 (d, J=8.8 Hz, 2 H), 3.63 (s, br, 2 H); $^{13}$C NMR (CDCl$_3$) δ 144.90, 129.05, 123.05, 116.17.

Example 23

Carbazole (Table 2, Entry 14)

2,2'-Dibromobiphenyl (0.207 g, 1.00 mmol), (CyPF-t-Bu)PdCl$_2$ (7.30 mg, 1.00×10$^{-2}$ mmol), and LiNH$_2$ (0.230 g, 10.0 mmol) in 2.0 mL DME gave 0.107 g (64%) of Carbazole as a solid (hexane/ethyl acetate: 70/30). $^1$H NMR (CDCl$_3$) δ 8.08 (d, J=7.6 Hz, 2 H), 7.99 (s, br, 1 H), 7.39-7.44 (m, 4 H), 7.21-7.27 (m, 2 H); $^{13}$C NMR (CDCl$_3$) δ 139.43, 125.81, 123.31, 120.31, 119.41, 110.54.

Example 24

Optimiztion of the Conditions of the Amination Reaction Using 4-t-Butylphenyl Bromide and Ammonia The reaction conditions were optimized for the amination reaction of using 4-t-butylphenyl bromide using ammonia. The reaction of 4-t-butylphenyl bromide was selected for optimization as reactions of unhindered arylating agents were considered most challenging since unhindered arylating agents are expected to be more likely to undergo further reaction to form the diarylamine instead of the aromatic primary amine.

(a) Stoichiometry of the Reaction with Ammonia.

The amination of 4-t-butylphenyl bromide (0.2M) in 1,2-dimethoxyethane with ammonia catalyzed by (CyPF-t-Bu)PdCl$_2$ (1.0 mol %), in the presence of sodium t-butoxide was performed using various concentrations of ammonia, and the conversion and amount of mono- and di-arylation products determined by $^1$H NMR of the crude reaction products. The results of the experiments are summarized in Table 3. The results show that selectivity for mono- versus di-arylation is improved by using greater concentrations of ammonia.

TABLE 3

Optimiztion of the Stoichimetry for the Catalyzed Amination Reaction using 4-t-Butylphenyl bromide and Ammonia.[a]

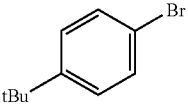

| Entry | Amount of NH$_3$ | Conditions | Conversion[b] (%) | Ratio[b] (A/B) |
|---|---|---|---|---|
| 1 | 22 equiv. | 80° C., 6 h | 70 | 2.3:1 |
| 2 | 44 equiv. | 80° C., 6 h | 95 | 5.4:1 |
| 3 | 66 equiv. | 80° C., 6 h | 95 | 8.9:1 |
| 4 | 66 equiv. | 80° C., 24 h | 100 | 9.5:1 |

[a]Reactions conducted at 0.2M with 1.0 mol % of Pd(CyPF-t-Bu)Cl$_2$, in sealed thick-wall NMR tubes;.
[b]Determined by $^1$H NMR of the crude product.

(b) Optimization of the Solvent.

The amination of 4-t-butylphenyl bromide (0.2M) with ammonia (66 eq.) catalyzed by (CyPF-t-Bu)PdCl$_2$ (1.0 mol %), in the presence of sodium t-butoxide was performed in various solvents, and the conversion and amount of mono- and di-arylation products determined by $^1$H NMR of the crude reaction products. The results of the experiments are summarized in Table 4. The results show that the reaction could be performed in a variety of solvents, although the reaction in DME gave the best selectivity.

TABLE 4

Optimiztion of the Solvent for the Catalyzed Amination Reaction using 4-t-Butylphenyl bromide and Ammonia.[a]

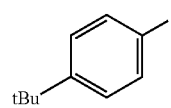

| Entry | Solvent | Conditions | Conversion[b] (%) | Ratio[b] (A/B) |
|---|---|---|---|---|
| 1 | DME | 80° C., 6 h | 95 | 8.9:1 |
| 2 | DME | 80° C., 24 h | 100 | 9.5:1 |
| 3 | THF | 80° C., 6 h | 0 | — |
| 4 | Toluene | 80° C., 6 h | 100 | 6.3:1 |
| 5 | 1,4-Dioxane | 80° C., 6 h | 100 | 8.2:1 |

[a]Reactions conducted at 0.2M with 1.0 mol % of Pd(CyPF-t-Bu)Cl$_2$, in sealed thick-wall NMR tubes;.
[b]Determined by $^1$H NMR of the crude product.

(c) Optimization of the Reaction Concentration.

The amination of 4-t-butylphenyl bromide with ammonia catalyzed by (CyPF-t-Bu)PdCl$_2$ (1.0 mol %), in the presence of sodium t-butoxide (3 eq.) in DME was performed at various concentrations. The reaction was performed in a Parr bomb with the reaction mixture saturated with ammonia by stirring at ambient temperature for 30 min under 80 p.s.i. of ammonia before commencing heating. The reaction mixture was then heated at 90° C. The conversion and amount of mono- and di-arylation products determined by $^1$H NMR of the crude reaction products. The results of the experiments are summarized in Table 5. The results show that the reaction selectivity was optimized by increasing the dilution of the reaction. However, this was not necessary for hindered substrates, which underwent the amination reaction with excellent selectivity (see Table 1 above).

TABLE 5

Optimiztion of the Solvent for the Catalyzed Amination Reaction using 4-t-Butylphenyl bromide and Ammonia.[a]

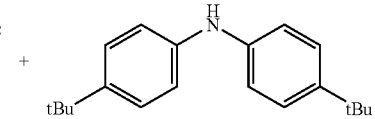

| Entry | Concentration | Conditions | Conversion[b] (%) | Ratio[b] (A/B) | Yield[c] (%) |
|---|---|---|---|---|---|
| 1 | 0.05M | 90° C., 24 h | 100 | 35:1 | 88 |
| 2 | 0.1M | 90° C., 24 h | 100 | 14.4:1 | 82 |
| 3 | 0.2M | 90° C., 20 h | 100 | 9.63:1 | 71 |

[a]Reactions conducted at 0.2M with 1.0 mol % of Pd(CyPF-t-Bu)Cl$_2$, in sealed thick-wall NMR tubes;.
[b]Determined by $^1$H NMR of the crude product;
[c]Isolated yield of A.

Example 25

Optimization of the Ligand in the Palladium-Catalyzed Amination Reaction of 4-t-Butylphenyl Bromide with Ammonia The amination of 4-t-butylphenyl bromide with ammonia in the presence of sodium t-butoxide in DME was performed using various palladium catalysts (1.0 mol %)—either a preformed palladium-phosphine complex or a complex formed in situ using [bis-di(benzylidene)acetone]palladium (0) and a ligand (either a phosphine or a carbene ligand). The reaction was performed in a Parr bomb with the reaction mixture saturated with ammonia by stirring at ambient temperature for 30 min under 80 p.s.i. of ammonia before commencing heating. The reaction mixture was then heated at 80° C. The conversion and amount of mono- and di-arylation products was determined by $^1$H NMR of the crude reaction products. The results of the experiments are summarized in Table 6. Only reaction with ligands of the formula I achieved the desired conversion to an aromatic primary amine, with preformed (CyPF-t-Bu)PdCl$_2$ giving the better selectivity.

TABLE 6

Optimiztion of the Ligand for the Catalyzed Amination Reaction using 4-t-Butylphenyl bromide and Ammonia.

| Entry | Pd-Ligand | Conversion$^a$ (%) | Ratio$^a$ (A/B) |
|---|---|---|---|
| 1 | (CyPF-t-Bu)PdCl$_2$ | 100 | 9.5:1 |
| 2 | Pd(dba)$_2$/PPF-t-Bu | 100 | 1:1 |
| 3 | Pd(BINAP)$_2$ | 0 | — |
| 4 | (DPPF)PdCl$_2$ | 0 | — |
| 5 | [tBu$_3$PPdBr]$_2$ | 0 | — |
| 6 | Pd(dba)$_2$/Q-phos | 0 | — |
| 7 | Pd(dba)$_2$/X-Phos | 0 | — |
| 8 | Pd(dba)$_2$/IPr | 0 | — |

Ligands Used:

DPPF

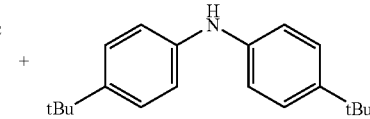

BINAP

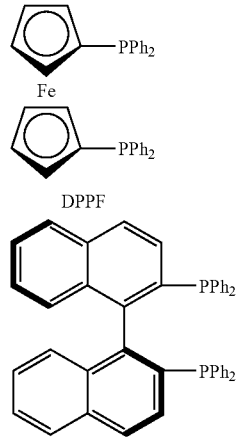

X-Phos

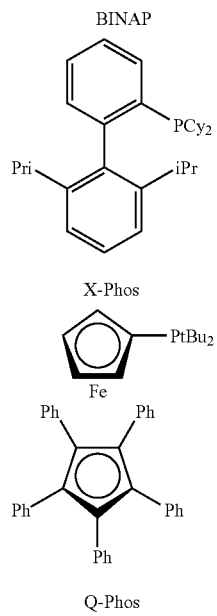

Q-Phos

TABLE 6-continued

Optimiztion of the Ligand for the Catalyzed Amination Reaction using 4-t-Butylphenyl bromide and Ammonia.

R = Ph, PPF-t-Bu
Cy, CyPF-t-bu

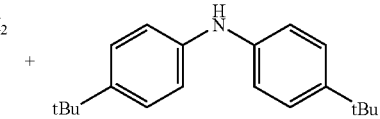

IPr $^a$Determined by $^1$H NMR of the crude product.

Example 26

Optimization of the Conditions for the Catalyzed Amination Reaction of A Base-Sensitive Aryl Halide with Ammonia A series of experiments was performed to determine whether milder bases than sodium t-butoxide can be used in the catalyzed ammoniation reaction of ammonia with an aryl halide. For this purpose, the ammoniation of ethyl 4-bromobenzoate was studied. For the reaction of an unhindered ester (such as ethyl 4-bromobenzoate) the reaction conditions using strong bases (such as sodium t-butoxide or lithium amide) are not suitable, so this substrate was studied to determine whether milder bases may be used.

The results of a series of experiments in which ethyl 4-bromobenzoate was subjected to a catalyzed ammoniation reaction with ammonia catalyzed by (CyPF-t-Bu)PdCl$_2$ formed in situ using palladium (II) acetate (1.0 mol %) and the ligand (1.0 mol %) in DME in the presence of various bases (2 eq.) are summarized in Table 7. As demonstrated by the data in Table 7, both cesium carbonate and tribasic potassium phosphate could be used successfully in the ammoniation reaction of ethyl 4-bromobenzoate to give ethyl 4-aminobenzoate.

TABLE 7

Optimiztion of the Base for the Catalyzed Amination Reaction using Ethyl 4-Bromobenzoate and Ammonia.

| Entry | Base | Reaction Conditions | Conversion[a] (%) | Ratio[b] (C/D) | Yield[a] (%) |
|---|---|---|---|---|---|
| 1 | NaOtBu | 0.17M, 70° C., 12 h | 100 | — | 0 |
| 2 | Cs$_2$CO$_3$ | 0.17M, 70° C., 12 h | 100 | 5.7:1 | 74 |
| 3 | Cs$_2$CO$_3$ | 0.08M, 70° C., 12 h | 98 | 6:1 | 75 |
| 4 | Cs$_2$CO$_3$ | 0.17M, 90° C., 12 h | 100 | ND | 45 |
| 5 | K$_3$PO$_4$ | 0.17M, 70° C., 12 h | 30 | — | 30 |
| 6 | K$_3$PO$_4$ | 0.17M, 90° C., 12 h | 98 | 0.7:1 | 35 |
| 7[c] | K$_3$PO$_4$[c] | 0.10M, 70° C., 24 h | 100 | — | 100 |

[a]Conversion and yield determined by GC using dodecane as an internal standard;.
[b]Determined by $^1$H NMR of the crude product;
[c]5 eq. of K$_3$PO$_4$ and 2 mol% of catalyst used.

Example 27

Optimiztion of the Conditions of the Amination Reaction using 4-t-Butylphenyl Bromide and Lithium Amide The optimization of the reaction conditions for the lithium amide reaction was performed, as with the ammonia reaction, using 4-t-butylphenyl bromide. The amination of 4-t-butylphenyl bromide with lithium amide catalyzed by (CyPF-t-Bu)PdCl$_2$ (1.0 mol %) was performed using various amounts of lithium amide, in various solvents, at various temperatures, and for various times. The conversion and the ratio of mono- to di-arylation products were determined by $^1$H NMR of the crude reaction products. The results of these experiments are summarized in Table 8. The selectivites improved at higher dilution, with reactions conducted with a 0.05 M concentration of the 4-t-butylphenyl bromide giving the highest selectivity. Selectivity was also improved by the use of a greater excess of lithium amide, although using 10-fold excess gave good selectivity at 0.05M. The reaction proceeded in 1,2-dimethoxyethane (DME), tetrahydrofuran (THF) and 1,4-dioxane, with 1,2-dimethoxyethane giving the best results. Finally, a detrimental effect of increased temperature was observed on selectivity, with lower selectivity being observed when the reaction was conducted at 110° C., in contrast to better selectivity at 110° C.

TABLE 8

Optimiztion of the Stoichimetry for the Catalyzed Amination Reaction using 4-t-Butylphenyl bromide and Lithium Amide.

| Entry | Concentration | Amount of LiNH$_2$ | Solvent | Reaction Conditions | Conversion[a] (%) | Ratio[a] (A/B) | Yield[b] (%) |
|---|---|---|---|---|---|---|---|
| 1 | 0.2M | 5 equiv. | DME | 80° C., 10 h | 100 | 4.6:1 | — |
| 2 | 0.2M | 10 equiv. | DME | 80° C., 10 h | 100 | 5.6:1 | — |
| 3 | 0.2M | 20 equiv. | DME | 80° C., 10 h | 100 | 7.8:1 | — |
| 4 | 0.2M | 50 equiv. | DME | 80° C., 10 h | 100 | 9.4:1 | — |
| 5 | 0.1M | 10 equiv. | DME | 80° C., 10 h | 100 | 6.7:1 | — |
| 6 | 0.05M | 10 equiv. | DME | 80° C., 10 h | 100 | 9.5:1 | 72 |
| 7 | 0.05M | 10 equiv. | DME | 110° C., 6 h | 100 | 1:2.3 | — |
| 8 | 0.05M | 10 equiv. | THF | 80° C., 24 h | 100 | 6.6:1 | — |
| 9 | 0.05M | 10 equiv. | Diioxane | 80° C., 24 h | 100 | 10.9:1 | 37 |

[a]Determined by $^1$H NMR of the crude product; Isolated yield of A.

Example 28

Optimization of the Ligand in the Catalyzed Amination Reaction of 4-t-Butylphenyl Bromide with Lithium Amide The amination of 4-t-butylphenyl bromide with ammonia in the presence of sodium t-butoxide in DME was performed at using various palladium catalysts (1.0 mol %)—either a pre-formed palladium-phosphine complex or a complex formed in situ using [bis-di(benzylidene)acetone]palladium (0) and the phosphine ligand. The reaction mixture was then heated at 80° C. for 24 h. The conversion and amount of mono- and di-arylation products was determined by $^1$H NMR of the crude reaction products. The results of the experiments are summarized in Table 9. Only reaction with ligands of the formula I achieved the desired conversion to an aromatic primary amine (Entries 1 and 2), with pre-formed (CyPF-t-Bu)PdCl$_2$ giving the better selectivity.

TABLE 9

Optimiztion of the Ligand for the Catalyzed Amination Reaction using 4-t-Butylphenyl bromide and Ammonia.

| Entry | Pd-Ligand | Conversion$^a$ (%) | Ratio$^a$ (A/B) |
|---|---|---|---|
| 1 | (CyPF-t-Bu)PdCl$_2$ | 100 | 9.5:1 |
| 2 | Pd(dba)$_2$/PPF-t-Bu | 100 | 1:1 |
| 3 | Pd(BINAP)$_2$ | 0 | — |
| 4 | (DPPF)PdCl$_2$ | 0 | — |
| 5 | [tBu$_3$PPdBr]$_2$ | 0 | — |
| 6 | Pd(dba)$_2$/Q-phos | 0 | — |
| 7 | Pd(dba)$_2$/X-Phos | 0 | — |

Ligands Used:

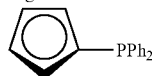

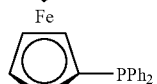

DPPF

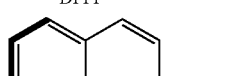

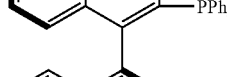

BINAP

TABLE 9-continued

Optimiztion of the Ligand for the Catalyzed Amination Reaction using 4-t-Butylphenyl bromide and Ammonia.

X-Phos

Q-Phos

R = Ph, PPF-t-Bu
Cy, CyPF-t-bu
$^a$Determined by $^1$H NMR of the crude product.

Example 29

Demonstration of the Beneficial Effect of Zinc Chloride in Promoting the Catalyzed Amination of 3-Bromoanisole with Lithium Amide The advantageous effect of adding zinc chloride to an amination reaction was demonstrated in the amination reaction of 3-bromoanisole, the results of which are summarized in Table 10. When 3-bromoanisole was reacted under the standard lithium amide amination conditions, using lithium amide (10 eq.) in the presence of (CyPF-t-Bu)PdCl$_2$ (1 mol %) in DME gave a complicated mixture of products was obtained (Table 10, Entry 1). When conducted in the presence of zinc chloride and TMEDA, however, the reaction could successfully gave the desired monoarylation product, 3-methoxyaniline, although at high concentrations N,N-dimethyl-3-methoxyaniline was formed in a significant amount as a by-product (Table 10, Entries 3 and 4). Under optimized conditions (Table 10, Entries 8 and 9), 3-methoxyaniline was formed selectively in good yield.

The crystals were filtered and washed with pentane and dried under vacuum to give 356 mg (84%) of a single isomer of the product. $^1$H NMR (CDCl$_3$) δ 0.80-2.80 (m, 22 Cy H), 1.16 (d, J=12.8 Hz, 9 H), 1.66 (d, J=11.6 Hz, 9 H), 1.80-1.84 (m, 4 H from THF), 1.96 (t, J=7.6 Hz, 3 H), 3.17 (dq, J=6.0, 5.6 Hz, 1 H), 3.74 (s, 3 H), 3.71-3.76 (m, 4 H from THF), 4.23 (s, 5 H), 4.30 (t, J=2.4 Hz, 1 H), 4.49 (s, br, 1 H), 4.85 (s, br, 1 H), 6.55 (d, J=7.2 Hz, 1 H), 6.77 (d, J=6.8 Hz, 1 H), 7.10-7.25 (s, br, 1 H), 7.25-7.40 (s, br, 1 H); $^{31}$P {$^1$H} NMR (CH$_2$Cl$_2$, −30° C.)

TABLE 10

Use of Zinc Chloride in Promoting the Catalyzed Amination of 3-Bromoanisole with Lithium Amide

| Entry | LiNH$_2$$^a$ | ZnCl$_2$$^a$ | TMEDA$^a$ | Conc.$^b$ (M) | Conversion (%)$^c$ | 2/3$^d$ | 2/4$^d$ | Yield$^e$ |
|---|---|---|---|---|---|---|---|---|
| 1 | 10 | 0 | 0 | 0.50 | 100 | — | — | n/d$^f$ |
| 2 | 10 | 1 | 0 | 0.50 | 100 | — | — | n/d$^g$ |
| 3 | 10 | 1 | 1 | 0.50 | 100 | trace 3 | 1.7/1.0 | — |
| 4 | 10 | 1 | 1 | 0.20 | 100 | trace 3 | 2.4/1.0 | 24 |
| 5 | 10 | 1 | 1 | 0.05 | 100 | 1.16/1.0 | 38.0/1.0 | — |
| 6 | 10 | 2 | 2 | 0.50 | <10 | trace 3 | — | <5% |
| 7 | 10 | 3 | 3 | 0.20 | 0 | — | — | — |
| 8 | 8 | 1 | 1 | 0.08 | 100 | trace 3 | 30/1.0 | 68 |
| 9 | 6 | 1 | 1 | 0.08 | 100 | trace 3 | >50/1 | 72 |

$^a$Number of equivalentx.
$^b$Concentration in Molarity.
$^c$Conversion determined by GC with dodecane as an internal standard.
$^d$Determined by $^1$H NMR spectroscopy.
$^e$Isolated yield after purification by flash column chromatography.
$^f$Multiple products were observed;
$^g$Multiple products were observed, including some of the desired aromatic primary amine.

Example 30

Stoichimetric Reactions of Palladium Complexes to Yield Aromatic Primary Amines

To show that a palladium species is involved in formation of the C—N bond, a stoichiometric reaction of Pd(CyPF-t-Bu)(4-MeOPh)(Br) with ammonia yielding a primary amine was performed.

(a) Preparation of (CyPF-t-Bu)Pd(4-MeOPh)(Br)

CyPF-t-Bu (0.277 g, 0.500 mmol) in 2.0 mL benzene was added to a mixture of Pd[P(o-Tol)$_3$]$_2$ (0.357 g, 0.500 mmol) and 4-bromoanisole (0.467 g, 5.00 mmol) in 20 ml benzene. The mixture was allowed to stir at room temperature for 30 min. The resulting red solution was filtered, and the solvent was evaporated under vacuum. The residue was redissolved in 2 mL THF. The THF solution was layered with pentane and cooled at −10° C. The product was deposited as red crystals. 72.83 (d, J=34.5 Hz), 18.08 (d, J=34.8 Hz); Anal. Calcd. For C$_{43}$H$_{67}$BrFeO$_2$P$_2$Pd.THF: C, 56.13; H, 7.34. Found: C, 56.35; H, 7.65.

(b) Stoichiometric Reactions of (CyPF-t-Bu)Pd(4-MeOPh)(Br) with Ammonia and NaOtBu (CyPF-t-Bu)Pd(4-MeOPh)(Br) (8.2 mg, 1.0×10$^{-3}$ mmol), NaOtBu (1.0 mg, 1.0×10$^{-3}$ mmol) and P(Ph-d$_5$)$_3$ (2.7 mg, 2.0×10$^{-3}$ mmol) were dissolved 0.5 mL C$_6$D$_6$ containing 1,3,5-trimethoxybenzene (0.29 mg, 1.7×10$^{-3}$ mmol). A $^1$H NMR spectrum was recorded. NH$_3$ (5.0 cm$^3$ at 0.1 atm pressure) was added by vacuum transfer. The tube was sealed and heated at 90° C. in a oil bath. $^{31}$P {$^1$H} NMR spectrometry showed the disappearance of the starting material and the formation of (CyPF-t-Bu)Pd P(Ph-d$_5$)$_3$. A $^1$H NMR spectrum was recorded, and the yield of 4-t-butylaniline and di(4-t-butylphenyl)amine as the monoarylation and diarylation products was determined by the integrating the aromatic C—H resonances of amines versus the internal standard. As determined by $^1$H NMR the arylation products were obtained in 80% yield with a 3:1 ratio of monoarylation to diarylation product by NMR spectroscopy.

Example 31

Preparation of an Arylpalladium-NH$_2$ Complex and Reductive Elimination from the Complex to Form an Arylation Product During the reaction described in Example 29, an intermediate was detected by $^{31}$P NMR spectroscopy that was believed to be an arylpalladium amido species as described in the catalytic cycle shown in Scheme 2, of a structure according to formula IV. In order to provide evidence for this hypothesis, an arylpalladium amide complex according to formula IV was prepared by an independent route, as described below.

(a) Preparation of [(CyPF-t-Bu)Pd(4-MeOPh)(NH$_3$)]OTf (CyPF-t-Bu)Pd(4-MeOPh)(Br) 1 (220 mg, 25.9 mmol) was dissolved in 5 mL of CH$_2$Cl$_2$ in a reaction tube sealed to a high vacuum valve. 50 cm$^3$ of ammonia at 0.3 atm pressure was condensed into the reaction tube by vacuum transfer. The tube was brought into the dry box AgOTf (66.0 mg, 25.9 mmol) was added. The solution turned cloudy immediately. After stirring at room temperature for 30 min, the solution was carefully decanted and filtered through a plug of diatomaceous earth ("Celite®"). The resulting solution was evaporated to approximately $\frac{1}{10}^{th}$ of the original volume. The solution was layered with toluene and allowed to stand at −35° C. overnight. The product was isolated as a pale yellow powder. Crystals suitable for X-ray diffraction was obtained by slow crystallization of a toluene solution of the complex at room temperature. $^1$H NMR (THF-d$_8$, −30° C.) δ 7.48-7.56 (m, 1 H), 7.05-7.22 (m, 1 H), 7.05-7.22 (m, from toluene), 6.80-6.90 (m, 1 H), 6.65-6.69 (m, 1 H), 5.07 (s, br, 0.74 H, major), 4.96 (s, br, 0.20 H from minor), 4.83 (s, br, 0.78 H from major), 4.68 (s, br, 0.27 H from minor), 4.63 (s, br, 1 H), 4.27 (s, 1 H from minor), 4.36 (s, 4 H from major), 3.70 (s, 3 H), 3.57-3.61 (m, 2.7 H from THF), 3.22-3.32 (m, 0.77 H from major), 3.06 (s, br, 0.21 H from minor), 2.94 (s, br, 0.62 H from minor), 2.74 (s, b, 2.37 H from major), 2.31 (s, 2.39 H from toluene), 2.03 (t, J=7.6 Hz, 3 H), 1.56 (d, J=11.6 Hz, 9 H), 1.05 (d, J=11.6 Hz, 9 H), 0.80-2.50 (m, 22 Cy H); $^{31}$P {$^1$H} NMR (THF-d$_8$, −30° C.) 70.96 (d, J=29.1 Hz, major), 68.74 (d, J=27.5 Hz, minor), 25.82 (d, J=27.5 Hz, minor), 20.12 (d, J=29.1 Hz, major). IR: ν(NH$_3$) 3088, 3172, 3255, 3321, 3364 cm$^{-1}$. Anal. Calcd. For C$_{40}$H$_{62}$F$_3$FeNO$_4$P$_2$Pd·0.8 equiv. of toluene: C, 54.34; H, 6.83; N, 1.39. Found: C, 54.16; H, 6.50; N, 1.32.

(b) Preparation of (CyPF-t-Bu)Pd(4-MeOPh)(NH$_2$)

[(CyPF-t-Bu)Pd(4-MeOPh)(NH$_3$)]OTf (147 mg, 0.150 mmol) was dissolved in 5 mL of THF. KN(SiMe$_3$)$_2$ (33.0 mg, 0.160 mmol) was added to the stirred solution as a solid. The reaction was allowed to stir at room temperature for 30 min, and it turned to a slightly pale yellow-green color. The solvent was evaporated under vacuum. The resulting solid was dissolved in 3 mL benzene. The benzene solution was filtered through a plug of diatomaceous earth ("Celite®"), and benzene was evaporated under vacuum. The solid was dissolved in 1 mL THF and was layered with pentane. Pure yellow crystals (47.0 mg, 40%) were obtained by cooling the layered solution at −35° C. for two days. $^1$H NMR (C$_6$D$_6$) δ 7.88 (br, 1 H), 7.64 (br, 1 H), 7.04 (d, J=7.2 Hz, 1 H), 6.94 (d, J=6.0 Hz, 1 H), 4.56 (s, br, 1 H), 4.06 (s, br, 1 H), 4.01 (s, 6 H), 3.55-3.57 (m, 0.4 H from THF), 3.48 (s, 3 H), 3.00-3.10 (m, 1 H), 1.69 (t, J=6.8 Hz, 3 H), 1.56 (d, J=10.8 Hz, 9 H), 1.30 (d, J=12.8 Hz, 9 H), 0.80-2.5 (m, 22 Cy H), 0.47 (s, br, 2 H); $^{31}$P {$^1$H} NMR (THF-d8, −30° C.) 65.03 (d, J=31.9 Hz, major), 64.74 (d, J=30.1 Hz, minor), 17.98 (d, J=30.8 Hz, minor), 11.45 (d, J=30.8 Hz, major). IR: ν(NH$_2$) 3278, 3356 cm$^{-1}$. Suitable elemental analysis was not obtained because the compound decomposes at room temperature as a solid over a 12-24 h time period.

(c) Reductive Elimination Reaction from (CyPF-t-Bu)Pd(4-MeOPh)(NH$_2$)

(CyPF-t-Bu)Pd(4-MeOPh)(NH$_2$) (8.2 mg, 1.0×10$^{-3}$ mmol) and P(Ph-d$_5$)$_3$ (2.7 mg, 2.0×10$^{-3}$ mmol) were dissolved 0.5 mL C$_6$D$_6$ containing 1,3,5-trimethoxybenzene (0.29 mg, 1.7×10$^{-3}$ mmol). A $^1$H NMR spectrum was recorded. The tube was sealed and heated at 90° C. in a oil bath. $^{31}$P {$^1$H} NMR spectrometry showed the disappearance of the starting material and the formation of (CyPF-t-Bu)PdP(Ph-d$_5$)$_3$. A $^1$H NMR spectrum was recorded, and the yield of 4-t-butylaniline and di(4-t-butylphenyl)amine was determined by integrating the aromatic C—H resonances of amines versus the internal standard.

All references cited herein are incorporated by reference. The present invention may be embodied in other specific forms without departing from the spirit or essential attributes thereof and, accordingly, reference should be made to the appended claims, rather than to the foregoing specification, as indicating the scope of the invention.

What is claimed is:

1. A process for preparing an aromatic primary amine, said aromatic primary amine comprising an amino group attached to an aromatic ring, said process comprising reacting:

(a) an arylating agent comprising a leaving group attached to an aromatic ring; and (b) an ammoniating agent selected from the group consisting of:

(i) ammonia; and (ii) a metal amide;

in a composition comprising a complex comprising:

(a) a Group VIII metal atom or ion; and (b) a ligand, wherein the ligand is a compound of formula I:

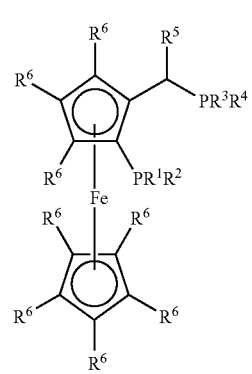

wherein:

R$^1$ and R$^2$ are independently selected from the group consisting of (C$_1$-C$_{12}$)alkyl, (C$_1$-C$_{12}$)heteroalkyl, and optionally substituted aromatic rings, or —PR$^1$R$^2$ is a radical of the formula II:

(II)

[Structure of formula II: aromatic rings α and β fused with P center, with attachment point]

wherein α and β are optionally substituted aromatic rings;

$R^3$ and $R^4$ are independently selected from the group consisting of $(C_1-C_{12})$alkyl, $(C_1-C_{12})$heteroalkyl, and optionally substituted aromatic rings, or —$PR^3R^4$ is a radical of the formula II;

$R^5$ is selected from the group consisting of hydrogen, $(C_1-C_8)$alkyl, $(C_1-C_8)$heteroalkyl and optionally substituted aromatic rings, each $R^6$ is independently selected from the group consisting of hydrogen, and $(C_1-C_4)$alkyl;

wherein each of said optionally substituted aromatic rings is either unsubstituted or substituted at any substitutable position with one or more substituents independently selected from the group consisting of $(C_1-C_4)$alkyl, $(C_1-C_4)$heteroalkyl, $(C_1-C_3)$ fluorinated alkyl, —$OR^7$, —$SR^7$, and $NR^7_2$;

each $R^7$ is independently selected from the group consisting of $(C_1-C_4)$alkyl and $(C_1-C_4)$heteroalkyl, or, within any occurrence of $NR^7_2$, independently of any other occurrence of $NR^7_2$ the two $R^7$ groups in combination form $(C_4-C_8)$alkylene or $(C_4-C_8)$heteroalkylene;

or any one occurrence of $R^6$, or any one substitutable position of any one of the groups $R^1$, $R^2$, $R^3$, $R^4$, $R^5$ and $R^7$, is a point of attachment, directly or via a tethering group, to a polymer or a solid phase support;

provided that when the ammoniating agent is ammonia, the composition comprising the complex further comprises a base;

whereby the leaving group of the arylating agent is substituted by an amino group to form the aromatic primary amine.

2. A process according to claim 1, wherein the Group VIII metal is selected from the group consisting of nickel, palladium and platinum.

3. A process according to claim 1, wherein the Group VIII metal is palladium.

4. A process according to claim 3, wherein the leaving group is a halogen selected from the group consisting of chloride, bromide and iodide.

5. A process according to claim 3, wherein the ammoniating agent is ammonia.

6. A process according to claim 5, wherein the base is selected from the group consisting of alkali metal alkoxides, carbonates, and phosphates.

7. A process according to claim 6, wherein the base is selected from the group consisting of sodium t-butoxide, cesium carbonate, and tribasic potassium phosphate.

8. A process according to claim 6, wherein the base is sodium t-butoxide.

9. A process according to claim 3, wherein the ammoniating agent is a metal amide.

10. A process according to claim 9, wherein the metal amide is an alkali metal amide.

11. A process according to claim 10, wherein the composition further comprises a zinc halide.

12. A process according to claim 9, wherein the alkali metal amide is lithium amide.

13. A process according to claim 12, wherein the composition further comprises zinc chloride.

14. A process according to claim 3, wherein $R^6$ is other than hydrogen at one or fewer occurrences.

15. A process according to claim 14, wherein each $R^6$ is hydrogen.

16. A process according to claim 14, wherein $R^5$ is hydrogen or methyl.

17. A process according to claim 15, wherein $R^5$ is methyl.

18. A process according to claim 14, wherein each of $R^3$ and $R^4$ is independently secondary or tertiary alkyl.

19. A process according to claim 17, wherein each of $R^3$ and $R^4$ is independently secondary or tertiary alkyl.

20. A process according to claim 19, wherein each of $R^3$ and $R^4$ is tertiary alkyl.

21. A process according to claim 20, wherein each of $R^3$ and $R^4$ is t-butyl.

22. A process according to claim 3, wherein the compound according to formula I is selected from the group consisting of 1-[2-(bis(3,5-dimethyl-4-methoxyphenyl)phosphino)ferrocenyl]ethyldicyclohexylphosphine, 1-[2-(bis(4-trifluoromethylphenyl)phosphino)ferrocenyl]ethyl-di-t-butylphosphine; 1-[2-(di(3,5-bis-trifluoromethylphenyl)phosphino)-ferrocenyl]ethyldi(3,5-dimethylphenyl)phosphine; 1-[2-(di(3,5-bis-trifluoromethylphenyl) phosphino)ferrocenyl]ethyldicyclohexylphosphine; 1-[2-(di-(3,5-dimethylphenyl)phosphino)ferrocenyl]ethylbis(3,5-dimethylphenyl)phosphine; 1-[2-(di-2-furylphosphino)ferrocenyl]ethyldi-3,5-xylyl phosphine; 1-[2-(dicyclohexylphosphino)ferrocenyl]-ethyldicyclohexylphosphine; 1-[2-(dicyclohexylphosphino)ferrocenyl]-ethyldiphenylphosphine; 1-[2-(dicyclohexylphosphino)ferrocenyl]ethyldi-t-butylphosphine; 1-[2-(diphenylphosphino)ferrocenyl]ethyldi(3,5-dimethylphenyl)phosphine; 1-[2-(diphenylphosphino)ferrocenyl]-ethyldicyclohexylphosphine; 1-[2-(diphenylphosphino)ferrocenyl]-ethyldicyclohexylphosphine; 1-[2-(diphenylphosphino)ferrocenyl]-ethyldiphenylphosphine; 1-[2-(diphenylphosphino)fenocenyl]ethyldi-t-butylphosphine; 1-[2-(di-p-tolylphosphino)ferrocenyl]-ethyldicyclohexylphosphine; 1-[2-(di-t-butylphosphino)ferrocenyl]-ethyldiphenylphosphine.; (R)-1-[(S)-2-(bis(3,5-dimethyl-4-methoxyphenyl)phosphino)ferrocenyl] ethyldicyclohexylphosphine; (R)-1-[(S)-2-(bis(4-trifluoromethylphenyl)phosphino)ferrocenyl]ethyl-di-t-butylphosphine; (R)-1-[(S)-2-(di(3,5-bis-trifluoromethylphenyl)-phosphino)ferrocenyl]ethyldi(3,5-dimethylphenyl)phosphine; (R)-1-[(S)-2-(di(3,5-bis-trifluoromethylphenyl)phosphino)ferrocenyl]-ethyldicyclohexylphosphine; (R)-1-[(S)-2-(di-(3,5-dimethylphenyl)-phosphino)ferrocenyl]ethylbis(3,5-dimethylphenyl)phosphine; (R)-1-[(S)-2-(di-2-furylphosphino)ferrocenyl]ethyldi-3,5-xylyl phosphine; (R)-1-[(S)-2-(dicyclohexylphosphino)ferrocenyl] ethyldicyclohexylphosphine; (R)-1-[(S)-2-(dicyclohexylphosphino)ferrocenyl] ethyldiphenylphosphine; (R)-1-[(S)-2-(dicyclohexylphosphino)ferrocenyl]ethyldi-t-butylphosphine; (R)-1-[(S)-2-(diphenylphosphino)ferrocenyl]ethyldi(3,5-dimethylphenyl)-phosphine; (R)-1-[(S)-2-(diphenylphosphino)ferrocenyl]-ethyldicyclohexylphosphine; (R)-1-[(S)-2-(diphenylphosphino)ferrocenyl]-ethyldicyclohexylphosphine; (R)-1-[(S)-2-(diphenylphosphino)ferrocenyl]-ethyldiphenylphosphine; (R)-1-[(S)-2-(diphenylphosphino)ferrocenyl]-ethyldi-t-butylphosphine; (R)-1-[(S)-2-(di-p-tolylphosphino)ferrocenyl]-ethyldicyclohexylphosphine; (R)-1-[(S)-2-(di-t-butylphosphino)-ferrocenyl]ethyldiphenylphosphine; (S)-1-[(R)-2-(bis(3,5-dimethyl-4-methoxyphenyl)phosphino) ferrocenyl]ethyldicyclohexylphosphine; (S)-1-[(R)-2-(bis(4-trifluoromethylphenyl)phosphino)ferrocenyl]ethyl-di-t-butylphosphine; (S)-1-[(R)-2-(di(3,5-bis-trifluoromethylphenyl)-phosphino)ferrocenyl]ethyldi(3,5-dimethylphenyl)phosphine; (S)-1-[(R)-2-(di(3,5-bis-trifluoromethylphenyl)phosphino)ferrocenyl]-ethyldicyclohexylphosphine; (S)-1-[(R)-2-(di-(3,5-dimethylphenyl)-phosphino)ferrocenyl]ethylbis(3,5-dimethylphenyl)phosphine; (S)-1-[(R)-2-(di-2-furylphosphino)ferrocenyl]ethyldi-3,5-xylyl phosphine; (S)-1-[(R)-2-(dicyclohexylphosphino)ferrocenyl] ethyldicyclohexylphosphine; (S)-1-[(R)-2-(dicyclohexylphosphino)ferrocenyl] ethyldiphenylphosphine; (S)-1-[(R)-2-(dicyclohexylphosphino)ferrocenyl]ethyldi-t-butylphosphine; (S)-1-[(R)-2-(diphenylphosphino) ferrocenyl]ethyldi(3,5-dimethylphenyl)-phosphine; (S)-1-[(R)-2-(diphenylphosphino)ferrocenyl]-ethyldicyclohexylphosphine; (S)-1-[(R)-2-(diphenylphosphino)ferrocenyl]-ethyldicyclohexylphosphine; (S)-1-[(R)-2-(diphenylphosphino)ferrocenyl]-ethyldiphenylphosphine; (S)-1-[(R)-2-(diphenylphosphino)ferrocenyl]-ethyldi-t-butylphosphine; (S)-1-[(R)-2-(di-p-tolylphosphino)ferrocenyl]-ethyldicyclohexylphosphine; and (S)-1-[(R)-2-(di-t-butylphosphino)-ferrocenyl]ethyldiphenylphosphine.

23. A process according to claim 3, wherein the compound of formula I is selected from the group consisting of [2-(bis(3,5-dimethyl-4-methoxyphenyl)phosphino)ferrocenyl]methyldicyclohexylphosphine, [2-(bis(4-trifluoromethylphenyl)phosphino)ferrocenyl]methyl-di-t-butylphosphine; [2-(di(3,5-bis-trifluoromethylphenyl)phosphino)-ferrocenyl]methyldi(3,5-dimethylphenyl)phosphine; [2-(di(3,5-bis-trifluoromethylphenyephosphino)ferrocenyl]-methyldicyclohexylphosphine; [2-(di-(3,5-dimethylphenyl)phosphino)-ferrocenyl]methylbis(3,5-dimethylphenyl)phosphine; [2-(di-2-furylphosphino)ferrocenyl]ethyldi-3,5-xylyl phosphine; [2-(dicyclohexylphosphino)ferrocenyl]methyldicyclohexyphosphine; [2-(dicyclohexylphosphino)ferrocenyl]methyldiphenylphosphine; [2-(dicyclohexylphosphino)ferrocenyl]methyldi-t-butylphosphine; [2-(diphenylphosphino)ferrocenyl]methyldi(3,5-dimethylphenyl)phosphine; [2-(diphenylphosphino)ferrocenyl]methyldicyclohexylphosphine; [2-(diphenylphosphino)ferrocenyl]methyldicyclohexylphosphine; [2-(diphenylphosphino)ferrocenyl]methyldiphenylphosphine; [2-(diphenylphosphino)ferrocenyl]methyldi-t-butylphosphine; [2-(di-p-tolylphosphino)ferrocenyl]methyldicyclohexylphosphine; [2-(di-t-butylphosphino)ferrocenyl]methyldiphenylphosphine.; [(S)-2-(bis(3,5-dimethyl-4-methoxyphenyl)phosphino)ferrocenyl]-methyldicyclohexylphosphine; [(S)-2-(bis(4-trifluoromethylphenyl)-phosphino)ferrocenyl]methyl-di-t-butylphosphine; [(S)-2-(di(3,5-bis-trifluoromethylphenyl)phosphino)ferrocenyl]methyldi(3,5-dimethylphenyl)phosphine; [(S)-2-(di(3,5-bis-trifluoromethylphenyl)-phosphino)ferrocenyl]methyldicyclohexylphosphine; [(S)-2-(di-(3,5-dimethylphenyl)phosphino)ferrocenyl]methylbis(3,5-dimethylphenyl)-phosphine; [(S)-2-(di-2-furylphosphino)ferrocenyl]methyldi-3,5-xylyl phosphine; [(S)-2-(dicyclohexylphosphino)ferrocenyl]-methyldicyclohexylphosphine; [(S)-2-(dicyclohexylphosphino)ferrocenyl]-methyldiphenylphosphine; [(S)-2-(dicyclohexylphosphino)ferrocenyl]-methyldi-t-butylphosphine; [(S)-2-(diphenylphosphino)ferrocenyl]-methyldi(3,5-dimethylphenyl)phosphine; [(S)-2-(diphenylphosphino)-ferrocenyl]methyldicyclohexylphosphine; [(S)-2-(diphenylphosphino)-ferrocenyl] methyldicyclohexylphosphine; [(S)-2-(diphenylphosphino)-ferrocenyl]methyldiphenylphosphine; [(S)-2-(diphenylphosphino)-ferrocenyl]methyldi-t-butylphosphine; [(S)-2-(di-p-tolylphosphino)-ferrocenyl]methyldicyclohexylphosphine; [(S)-2-(di-t-butylphosphino)-ferrocenyl] methyldiphenylphosphine; [(R)-2-(bis(3,5-dimethyl-4-methoxyphenyl)phosphino)ferrocenyl] methyldicyclohexylphosphine; [(R)-2-(bis(4-trifluoromethylphenyl)phosphino)ferrocenyl]methyl-di-t-butylphosphine; [(R)-2-(di(3,5-bis-trifluoromethylphenyl) phosphino)-ferrocenyl]methyldi(3,5-dimethylphenyl) phosphine; [(R)-2-(di(3,5-bis-trifluoromethylphenyl) phosphino)ferrocenyl]-methyldicyclohexylphosphine; [(R)-2-(di-(3,5-dimethylphenyl)-phosphino)ferrocenyl]methylbis(3,5-dimethylphenyl)phosphine; [(R)-2-(di-2-furylphosphino)ferrocenyl]methyldi-3,5-xylyl phosphine; [(R)-2-(dicyclohexylphosphino)ferrocenyl]methyldicyclohexylphosphine; [(R)-2-(dicyclohexylphosphino)ferrocenyl] methyldiphenylphosphine; [(R)-2-(dicyclohexylphosphino) ferrocenyl]methyldi-t-butylphosphine; [(R)-2-(diphenylphosphino)ferrocenyl]methyldi(3,5-dimethylphenyl)phosphine; [(R)-2-(diphenylphosphino) ferrocenyl]methyldicyclohexylphosphine; [(R)-2-(diphenylphosphino)ferrocenyl] methyldicyclohexylphosphine; [(R)-2-(diphenylphosphino) ferrocenyl]methyldiphenylphosphine; [(R)-2-(diphenylphosphino)ferrocenyl]methyldi-t-butylphosphine; [(R)-2-(di-p-tolylphosphino)ferrocenyl]methyldicyclohexylphosphine; and [(R)-2-(di-t-butylphosphino)ferrocenyl]methyldiphenylphosphine.

24. A process according to claim 3, wherein the compound of formula I is selected from the group consisting of 1-[2-(dicyclohexylphosphino)-ferrocenyl]ethyldi-t-butylphosphine; 1-[2-(diphenylphosphino)ferrocenyl]-ethyldi-t-butylphosphine; (R)-1-[(S)-2-(dicyclohexylphosphino)-ferrocenyl]ethyldi-t-butylphosphine; (R)-1[(S)-2-(diphenylphosphino)-ferrocenyl]ethyldi-t-butylphosphine; (S)-1[(R)-2-(dicyclohexylphosphino)ferrocenyl]ethyldi-t-butylphosphine; and (S)-1-[(R)-2-(diphenylphosphino)ferrocenyl]ethyldi-t-butylphosphine.

25. A process according to claim 3, wherein the compound of formula I is 1-[2-(dicyclohexylphosphino)ferrocenyl]ethyldi-t-butylphosphine.

26. A process according to claim 3, wherein the compound of formula I is (R)-1-[(S)-2-(dicyclohexylphosphino)ferrocenyl]ethyldi-t-butylphosphine; (S)-1-[(R)-2-(dicyclohexylphosphino)ferrocenyl]ethyldi-t-butylphosphine; or the racemic mixture thereof.

27. A process according to claim 26, wherein the ammoniating agent is ammonia.

28. A process according to claim 27, wherein the base is sodium t-butoxide.

29. A process according to claim 26, wherein the ammoniating agent is an alkali metal amide.

30. A process according to claim 29, wherein the ammoniating agent is lithium amide.

31. A process according to claim 27, wherein the leaving group is selected from the group consisting of chloride, bromide, and iodide.

32. A process according to claim 28, wherein the leaving group is selected from the group consisting of chloride, bromide, and iodide.

33. A process according to claim 29, wherein the leaving group is selected from the group consisting of chloride, bromide, and iodide.

34. A process according to claim 30, wherein the leaving group is selected from the group consisting of chloride, bromide, and iodide.

35. A composition comprising:
(a) an ammoniating agent selected from the group consisting of:
    (i) ammonia; and
    (ii) a metal amide; and
(b) a complex comprising:
    (i) a Group VIII metal atom or ion; and
    (ii) a ligand, wherein the ligand is a compound of formula I:

(I)

wherein:
$R^1$ and $R^2$ are independently selected from the group consisting of $(C_1-C_{12})$alkyl, $(C_1-C_{12})$hetero alkyl, and optionally substituted aromatic rings, or —$PR^1R^2$ is a radical of the formula II:

(II)

wherein α and β are optionally substituted aromatic rings;
$R^3$ and $R^4$ are independently selected from the group consisting of $(C_1-C_{12})$alkyl, $(C_1-C_{12})$heteroalkyl, and optionally substituted aromatic rings, or —$PR^3R^4$ is a radical of the formula II;
$R^5$ is selected from the group consisting of hydrogen, $(C_1-C_8)$alkyl, $(C_1-C_8)$heteroalkyl and optionally substituted aromatic rings,
each $R^6$ is independently selected from the group consisting of hydrogen, and $(C_1-C_4)$alkyl;
wherein each of said optionally substituted aromatic rings is either unsubstituted or substituted at any substitutable position with one or more substituents independently selected from the group consisting of $(C_1-C_4)$alkyl, $(C_1-C_4)$heteroalkyl, $(C_1-C_3)$ fluorinated alkyl, —$OR^7$, —$SR^7$, and $NR^7_2$;
each $R^7$ is independently selected from the group consisting of $(C_1-C_4)$alkyl and $(C_1-C_4)$heteroalkyl, or, within any occurrence of $NR^7_2$, independently of any other occurrence of $NR^7_2$ the two $R^7$ groups in combination form $(C_4-C_8)$alkylene or $(C_4-C_8)$heteroalkylene;
or any one occurrence of $R^6$, or any one substitutable position of any one of the groups $R^1$, $R^2$, $R^3$, $R^4$, $R^5$ and $R^7$, is a point of attachment, directly or via a tethering group, to a polymer or a solid phase support;
provided that when the ammoniating agent is ammonia, the composition further comprises a base.

36. A composition according to claim 35, wherein the Group VIII metal is selected from the group consisting of nickel, palladium and platinum.

37. A composition according to claim 35, wherein the Group VIII metal is palladium.

38. A composition according to claim 37, wherein the ammoniating agent is ammonia.

39. A composition according to claim 38, wherein the base is selected from the group consisting of alkali metal alkoxides, carbonates, and phosphates.

40. A composition according to claim 39, wherein the base is selected from the group consisting of sodium t-butoxide, cesium carbonate, and tribasic potassium phosphate.

41. A composition according to claim 39, wherein the base is sodium t-butoxide.

42. A composition according to claim 37, wherein the ammoniating agent is a metal amide.

43. A composition according to claim 42, wherein the metal amide is an alkali metal amide.

44. A composition according to claim 43, further comprising a zinc halide.

45. A composition according to claim 43, wherein the alkali metal amide is lithium amide.

46. A composition according to claim 45, further comprising zinc chloride.

47. A composition according to claim 37, wherein $R^6$ is other than hydrogen at one or fewer occurrences.

48. A composition according to claim 47, wherein each $R^6$ is hydrogen.

49. A composition according to claim 47, wherein $R^5$ is hydrogen or methyl.

50. A composition according to claim 48, wherein $R^5$ is methyl.

51. A composition according to claim 47, wherein each of $R^3$ and $R^4$ is independently secondary or tertiary alkyl.

52. A composition according to claim 49, wherein each of $R^3$ and $R^4$ is independently secondary or tertiary alkyl.

53. A composition according to claim 51, wherein each of $R^3$ and $R^4$ is tertiary alkyl.

54. A composition according to claim 53, wherein each of $R^3$ and $R^4$ is t-butyl.

55. A composition according to claim 37, wherein the compound according to formula I is selected from the group consisting of 1-[2-(bis(3,5-dimethyl-4-methoxyphenyl)phosphino)ferrocenyl]ethyldicyclohexylphosphine, 1-[2-(bis(4-trifluoromethylphenyl)phosphino)ferrocenyl]ethyl-di-t-butylphosphine; 1-[2-(di(3,5-bis-trifluoromethylphenyl)phosphino)-ferrocenyl]ethyldi(3,5-dimethylphenyl)phosphine; 1-[2-(di(3,5-bis-trifluoromethylphenyl)phosphino)ferrocenyl]ethyldicyclohexylphosphine; 1-[2-(di-(3,5-dimethylphenyl)phosphino)ferrocenyl]ethylbis(3,5-dimethylphenyl)phosphine; 1-[2-(di-2-furylphosphino)ferrocenyl]ethyldi-3,5-xylyl phosphine; 1-[2-(dicyclohexylphosphino)ferrocenyl]-ethyldicyclohexylphosphine; 1-[2-(dicyclohexylphosphino)ferrocenyl]-ethyldiphenylphosphine; 1-[2-(dicyclohexylphosphino)ferrocenyl]ethyldi-t-butylphosphine; 1-[2-(diphenylphosphino)ferrocenyl]

ethyldi(3,5-dimethylphenyl)phosphine; 1-[2-(diphenylphosphino)ferrocenyl]-ethyldicyclohexylphosphine; 1-[2-(diphenylphosphino)ferrocenyl]-ethyldicyclohexylphosphine; 1-[2-(diphenylphosphino)ferrocenyl]-ethyldiphenylphosphine; 1-[2-(diphenylphosphino)ferrocenyl]ethyldi-t-butylphosphine; 1-[2-(di-p-tolylphosphino)ferrocenyl]-ethyldicyclohexylphosphine; 1-[2-(di-t-butylphosphino)ferrocenyl]-ethyldiphenylphosphine.; (R)-1-[(S)-2-(bis(3,5-dimethyl-4-methoxyphenyl)phosphino)ferrocenyl]ethyldicyclohexylphosphine; (R)-1-[(S)-2-(bis(4-trifluoromethylphenyl)phosphino)ferrocenyl]ethyl-di-t-butylphosphine; (R)-1-[(S)-2-(di(3,5-bis-trifluoromethylphenyl)-phosphino)ferrocenyl]ethyldi(3,5-dimethylphenyl)phosphine; (R)-1-[(S)-2-(di(3,5-bis-trifluoromethylphenyl)phosphino)ferrocenyl]-ethyldicyclohexylphosphine; (R)-1-[(S)-2-(di-(3,5-dimethylphenyl)-phosphino)ferrocenyl]ethylbis(3,5-dimethylphenyl)phosphine; (R)-1-[(S)-2-(di-2-furylphosphino)ferrocenyl]ethyldi-3,5-xylyl phosphine; (R)-1-[(S)-2-(dicyclohexylphosphino)ferrocenyl]ethyldicyclohexylphosphine; (R)-1-[(S)-2-(dicyclohexylphosphino)ferrocenyl]ethyl-diphenylphosphine; (R)-1-[(S)-2-(dicyclohexylphosphino)ferrocenyl]ethyldi-t-butylphosphine; (R)-1-[(S)-2-(diphenylphosphino)ferrocenyl]ethyldi(3,5-dimethylphenyl)-phosphine; (R)-1-[(S)-2-(diphenylphosphino)ferrocenyl]-ethyldicyclohexylphosphine; (R)-1-[(S)-2-(diphenylphosphino)ferrocenyl]-ethyldicyclohexylphosphine; (R)-1-[(S)-2-(diphenylphosphino)ferrocenyl]-ethyldiphenylphosphine; (R)-1-[(S)-2-(diphenylphosphino)ferrocenyl]-ethyldi-t-butylphosphine; (R)-1-[(S)-2-(di-p-tolylphosphino)ferrocenyl]-ethyldicyclohexylphosphine; (R)-1-[(S)-2-(di-t-butylphosphino)-ferrocenyl]ethyldiphenylphosphine; (S)-1-[(R)-2-(bis(3,5-dimethyl-4-methoxyphenyl)phosphino)ferrocenyl]ethyldicyclohexylphosphine; (S)-1-[(R)-2-(bis(4-trifluoromethylphenyl)phosphino)ferrocenyl]ethyl-di-t-butylphosphine; (S)-1-[(R)-2-(di(3,5-bis-trifluoromethylphenyl)-phosphino)ferrocenyl]ethyldi(3,5-dimethylphenyl)phosphine; (S)-1-[(R)-2-(di(3,5-bis-trifluoromethylphenyl)phosphino)ferrocenyl]-ethyldicyclohexylphosphine; (S)-1-[(R)-2-(di-(3,5-dimethylphenyl)-phosphino)ferrocenyl]ethylbis(3,5-dimethylphenyl)phosphine; (S)-1-[(R)-2-(di-2-furylphosphino)ferrocenyl]ethyldi-3,5-xylyl phosphine; (S)-1-[(R)-2-(dicyclohexylphosphino)ferrocenyl]ethyldicyclohexylphosphine; (S)-1-[(R)-2-(dicyclohexylphosphino)ferrocenyl]ethyldiphenylphosphine; (S)-1-[(R)-2-(dicyclohexylphosphino)ferrocenyl]ethyldi-t-butylphosphine; (S)-1-[(R)-2-(diphenylphosphino)ferrocenyl]ethyldi(3,5-dimethylphenyl)-phosphine; (S)-1-[(R)-2-(diphenylphosphino)ferrocenyl]-ethyldicyclohexylphosphine; (S)-1-[(R)-2-(diphenylphosphino)ferrocenyl]-ethyldicyclohexylphosphine; (S)-1-[(R)-2-(diphenylphosphino)ferrocenyl]-ethyldiphenylphosphine; (S)-1-[(R)-2-(diphenylphosphino)ferrocenyl]-ethyldi-t-butylphosphine; (S)-1-[(R)-2-(di-p-tolylphosphino)ferrocenyl]-ethyldicyclohexylphosphine; and (S)-1-[(R)-2-(di-t-butylphosphino)-ferrocenyl]ethyldiphenylphosphine.

56. A composition according to claim 37, wherein the compound of formula I is selected from the group consisting of [2-(bis(3,5-dimethyl-4-methoxyphenyl)phosphino)ferrocenyl]methyldicyclohexylphosphine, [2-(bis(4-trifluoromethylphenyl)phosphino)ferrocenyl]methyl-di-t-butylphosphine; [2-(di(3,5-bis-trifluoromethylphenyl)phosphino)-ferrocenyl]methyldi(3,5-dimethylphenyl)phosphine; [2-(di(3,5-bis-trifluoromethylphenyl)phosphino)ferrocenyl]-methyldicyclohexylphosphine; [2-(di-(3,5-dimethylphenyl)phosphino)-ferrocenyl]methylbis(3,5-dimethylphenyl)phosphine; [2-(di-2-furylphosphino)ferrocenyl]ethyldi-3,5-xylyl phosphine; [2-(dicyclohexylphosphino)ferrocenyl]methyldicyclohexylphosphine; [2-(dicyclohexylphosphino)ferrocenyl]methyldiphenylphosphine; [2-(dicyclohexylphosphino)ferrocenyl]methyldi-t-butylphosphine; [2-(diphenylphosphino)ferrocenyl]methyldi(3,5-dimethylphenyl)phosphine; [2-(diphenylphosphino)ferrocenyl]methyldicyclohexylphosphine; [2-(diphenylphosphino)ferrocenyl]methyldicyclohexylphosphine; [2-(diphenylphosphino)ferrocenyl]methyldiphenylphosphine; [2-(diphenylphosphino)ferrocenyl]methyldi-t-butylphosphine; [2-(di-p-tolylphosphino)ferrocenyl]methyldicyclohexylphosphine; [2-(di-t-butylphosphino)ferrocenyl]methyldiphenylphosphine.; [(S)-2-(bis(3,5-dimethyl-4-methoxyphenyl)phosphino)ferrocenyl]-methyldicyclohexylphosphine; [(S)-2-(bis(4-trifluoromethylphenyl)-phosphino)ferrocenyl]methyl-di-t-butylphosphine; [(S)-2-(di(3,5-bis-trifluoromethylphenyl)phosphino)ferrocenyl]methyldi(3,5-dimethylphenyl)phosphine; [(S)-2-(di(3,5-bis-trifluoromethylphenyl)-phosphino)ferrocenyl]methyldicyclohexylphosphine; [(S)-2-(di-(3,5-dimethylphenyl)phosphino)ferrocenyl]methylbis(3,5-dimethylphenyl)-phosphine; [(S)-2-(di-2-furylphosphino)ferrocenyl]methyldi-3,5-xylyl phosphine; [(S)-2-(dicyclohexylphosphino)ferrocenyl]-methyldicyclohexylphosphine; [(S)-2-(dicyclohexylphosphino)ferrocenyl]-methyldiphenylphosphine; [(S)-2-(dicyclohexylphosphino)-phino)ferrocenyl]-methyldi-t-butylphosphine; [(S)-2-(diphenylphosphino)ferrocenyl]-methyldi(3,5-dimethylphenyl)phosphine; [(S)-2-(diphenylphosphino)-ferrocenyl]methyldicyclohexylphosphine; [(S)-2-(diphenylphosphino)-ferrocenyl]methyldicyclohexylphosphine; [(S)-2-(diphenylphosphino)-ferrocenyl]methyldiphenylphosphine; [(S)-2-(diphenylphosphino)-ferrocenyl]methyldi-t-butylphosphine; [(S)-2-(di-p-tolylphosphino)-ferrocenyl]methyldicyclohexylphosphine; [(S)-2-(di-t-butylphosphino)-ferrocenyl]methyldiphenylphosphine; [(R)-2-(bis(3,5-dimethyl-4-methoxyphenyl)phosphino)ferrocenyl]methyldicyclohexylphosphine; [(R)-2-(bis(4-trifluoromethylphenyl)phosphino)ferrocenyl]methyl-di-t-butylphosphine; [(R)-2-(di(3,5-bis-trifluoromethylphenyl)phosphino)-ferrocenyl]methyldi(3,5-dimethylphenyl)phosphine; [(R)-2-(di(3,5-bis-trifluoromethylphenyl)phosphino)ferrocenyl]-methyldicyclohexylphosphine; [(R)-2-(di-(3,5-dimethylphenyl)-phosphino)ferrocenyl]methylbis(3,5-dimethylphenyl)phosphine; [(R)-2-(di-2-furylphosphino)ferrocenyl]methyldi-3,5-xylyl phosphine; [(R)-2-(dicyclohexylphosphino)ferrocenyl]methyldicyclohexylphosphine; [(R)-2-(dicyclohexylphosphino)ferrocenyl]methyldiphenylphosphine; [(R)-2-(dicyclohexylphosphino)ferrocenyl]methyldi-t-butylphosphine; [(R)-2-(diphenylphosphino)ferrocenyl]methyldi(3,5-dimethylphenyl)phosphine; [(R)-2-(diphenylphosphino)ferrocenyl]methyldicyclohexylphosphine; [(R)-2-(diphenylphosphino)ferrocenyl]methyldicyclohexylphosphine; [(R)-2-(diphenylphosphino)ferrocenyl]methyldiphenylphosphine; [(R)-2-(diphenylphosphino)ferrocenyl]methyldi-t-butylphosphine; [(R)-2-(di-p-tolyphosphino)ferrocenyl]methyldicyclohexylphosphine; and [(R)-2-(di-t-butylphosphino)ferrocenyl]methyldiphenylphosphine.

57. A composition according to claim 37, wherein the compound of formula I is selected from the group consisting of 1-[2-(dicyclohexylphosphino)-ferrocenyl]ethyldi-t-butylphosphine; 1-[2-(diphenylphosphino)ferrocenyl]-ethyldi-t-butylphosphine; (R)-1-[(S)-2-(dicyclohexylphosphino)-ferrocenyl]ethyldi-t-butylphosphine; (R)-1-[(S)-2-(diphenylphosphino)-ferrocenyl]ethyldi-t-butylphosphine; (S)-1-[(R)-2-(dicyclohexylphosphino)ferrocenyl]ethyldi-t-butylphosphine; and (S)-1-[(R)-2-(diphenylphosphino)ferrocenyl]ethyldi-t-butylpho sphine.

58. A composition according to claim 37, wherein the compound of formula I is 1-[2-(dicyclohexylphosphino)ferrocenyl]ethyldi-t-butylphosphine.

59. A composition according to claim 37, wherein the compound of formula I is (R)-1-[(S)-2-(dicyclohexylphosphino)ferrocenyl]ethyldi-t-butylphosphine; (S)-1-[(R)-2-(dicyclohexylphosphino)ferrocenyl]ethyldi-t-butylphosphine; or the racemic mixture thereof.

60. A composition according to claim 59, wherein the ammoniating agent is ammonia.

61. A composition according to claim 60, wherein the base is sodium t-butoxide.

62. A composition according to claim 59, wherein the ammoniating agent is an alkali metal amide.

63. A composition according to claim 62, wherein the ammoniating agent is lithium amide.

64. A transition metal complex according to the formula IV:

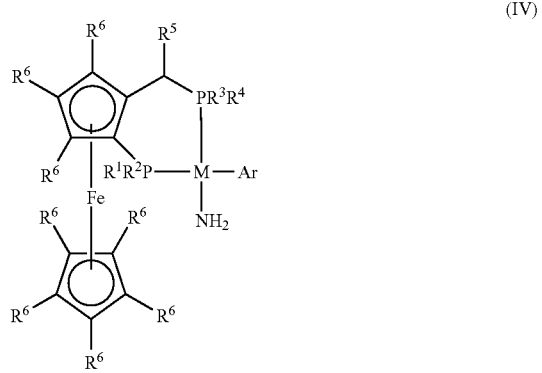

wherein:

M comprises a Group VIII metal atom or ion;

Ar represents a moiety comprising an aromatic ring wherein a carbon atom of the aromatic ring is sigma-bonded to the Group VIII metal atom or ion of M;

$R^1$ and $R^2$ are independently selected from the group consisting of $(C_1-C_{12})$alkyl, $(C_1-C_{12})$heteroalkyl, and optionally substituted aromatic rings, or —$PR^1R^2$ is a radical of the formula II:

wherein α and β are optionally substituted aromatic rings;

$R^3$ and $R^4$ are independently selected from the group consisting of $(C_1-C_{12})$alkyl, $(C_1-C_{12})$hetero alkyl, and optionally substituted aromatic rings, or —$PR^3R^4$ is a radical of the formula II;

$R^5$ is selected from the group consisting of hydrogen, $(C_1-C_8)$alkyl, $(C_1-C_8)$heteroalkyl and optionally substituted aromatic rings, each $R^6$ is independently selected from the group consisting of hydrogen, and $(C_1-C_4)$alkyl;

wherein each of said optionally substituted aromatic rings is either unsubstituted or substituted at any substitutable position with one or more substituents independently selected from the group consisting of $(C_1-C_4)$alkyl, $(C_1-C_4)$heteroalkyl, $(C_1-C_3)$ fluorinated alkyl, —OR, —$SR^7$, and $NR^7_2$;

each $R^7$ is independently selected from the group consisting of $(C_1-C_4)$alkyl and $(C_1-C_4)$heteroalkyl, or, within any occurrence of $NR^7_2$, independently of any other occurrence of $NR^7_2$ the two $R^7$ groups in combination form $(C_4-C_8)$alkylene or $(C_4-C_8)$heteroalkylene;

or any one occurrence of $R^6$, or any one substitutable position of any one of the groups $R^1$, $R^2$, $R^3$, $R^4$, $R^5$ and $R^7$, is a point of attachment, directly or via a tethering group, to a polymer or a solid phase support.

65. A transition metal complex according to claim 64, wherein the Group VIII metal is selected from the group consisting of nickel, palladium, and platinum.

66. A transition metal complex according to claim 64, wherein the Group VIII metal is palladium.

67. A transition metal complex according to claim 66, wherein $R^6$ is other than hydrogen at one or fewer occurrences.

68. A transition metal complex according to claim 67, wherein each $R^6$ is hydrogen.

69. A transition metal complex according to claim 67, wherein $R^5$ is hydrogen or methyl.

70. A transition metal complex according to claim 68, wherein $R^5$ is methyl.

71. A transition metal complex according to claim 67, wherein each of $R^3$ and $R^4$ is independently secondary or tertiary alkyl.

72. A transition metal complex according to claim 70, wherein each of $R^3$ and $R^4$ is independently secondary or tertiary alkyl.

73. A transition metal complex according to claim 72, wherein each of $R^3$ and $R^4$ is tertiary alkyl.

74. A transition metal complex according to claim 73, wherein each of $R^3$ and $R^4$ is t-butyl.

75. A transition metal complex according to claim 66 comprising a ligand selected from the group consisting of 1-[2-(bis(3,5-dimethyl-4-methoxyphenyephosphino)ferrocenyl]ethyldicyclohexylphosphine, 1-[2-(bis(4-trifluoromethylphenyl)phosphino)ferrocenyl]ethyl-di-t-butylphosphine; 1-[2-di(3,5-bis-trifluoromethylphenyl)phosphino)-ferrocenyl]ethyldi(3,5-dimethylphenyl)phosphine; 1-[2-(di(3,5-bis-trifluoromethylphenyl)phosphino)ferrocenyl]ethyldicyclohexylphosphine; 1-[2-(di-(3,5-dimethylphenyl)phosphino)ferrocenyl]ethylbis(3,5-dimethylphenyl)phosphine; 1-[2-(di-2-furylphosphino)ferrocenyl]ethyldi-3,5-xylyl phosphine; 1-[2-(dicyclohexylphosphino)ferrocenyl]-ethyldicyclohexylphosphine; 1-[2-(dicyclohexylphosphino)ferroceny]-ethyldiphenylphosphine; 1-[2-(dicyclohexylphosphino)ferrocenyl]ethyldi-t-butylphosphine; 1-[2-(diphenylphosphino)ferrocenyl]ethyldi(3,5-dimethylphenyl)phosphine; 1-[2-(diphenylphosphino)ferroceny]- ethyldicyclohexylphosphine; 1-[2-(diphenylphosphino)ferrocenyl]-ethyldicyclohexylphosphine; 1-[2-(diphenylphosphino)ferrocenyl]-ethyldiphenylphosphine; 1-[2-(diphenylphosphino)ferrocenyl]ethyldi-t-butylphosphine; 1-[2-(di-p-tolylphosphino)ferrocenyl]-ethyldicyclohexylphosphine; 1-[2-(di-t-butylphosphino)ferrocenyl]-ethyldiphenylphosphine.; (R)-1-[(S)-2-(bis(3,5-dimethyl-4-methoxyphenyl)phosphino)ferrocenyl]ethyldicyclohexylphosphine; (R)-1-[(S)-2-(bis(4-trifluoromethylphenyephosphino)ferrocenyl]ethyl-di-t-butylphosphine; (R)-1-[(S)-2-(di(3,5-bis-trifluoromethylphenyl)-phosphino)ferrocenyl]ethyldi(3,5-dimethylphenyl)phosphine; (R)-1-[(S)-2-(di(3,5-bis-trifluoromethylphenyephosphino)ferrocenyl]-ethyldicyclohexylphosphine; (R)-1-[(S)-2-(di-(3,5-dimethylphenyl)-phosphino)ferrocenyl]ethylbis(3,5-dimethylphenyl)phosphine; (R)-1-[(S)-2-(di-2-furylphosphino)ferrocenyl]ethyldi-3,5-xylyl phosphine; (R)-1-[(S)-2-(dicyclohexylphosphino)ferrocenyl]ethyldicyclohexylphosphine; (R)-1-[(S)-2-(dicyclohexylphosphino)ferrocenyl]ethyldiphenylphosphine; (R)-1-[(S)-2-(dicyclohexylphosphino)ferrocenyl]ethyldi-t-butylphosphine; (R)-1-[(S)-2-(diphenylphosphino)ferrocenyl]ethyldi(3,5-dimethylphenyl)-phosphine; (R)-1-[(S)-2-(diphenylphosphino)ferrocenyl]-ethyldicyclohexylphosphine; (R)-1-[(S)-2-(diphenylphosphino)ferrocenyl]-ethyldicyclohexylphosphine; (R)-1-[(S)-2-(diphenylphosphino)ferrocenyl]-ethyldiphenylphosphine; (R)-1-[(S)-2-(diphenylphosphino)ferrocenyl]-ethyldi-t-butylphosphine; (R)-1-[(S)-2-(di-p-tolylphosphino)ferrocenyl]-ethyldicyclohexylphosphine; (R)-1-[(S)-2-(di-t-butylphosphino)-ferrocenyl]ethyldiphenylphosphine; (S)-1-[(R)-2-(bis(3,5-dimethyl-4-methoxyphenyl)phosphino)ferrocenyl]ethyldicyclohexylphosphine; (S)-1-[(R)-2-(bis(4-trifluoromethylphenyl)phosphino)ferrocenyl]ethyl-di-t-butylphosphine; (S)-1-[(R)-2-(di(3,5-bis-trifluoromethylphenyl)-phosphino)ferrocenyl]ethyldi(3,5-dimethylphenyl)phosphine; (S)-1-[(R)-2-(di(3,5-bis-trifluoromethylphenyl)phosphino)ferrocenyl]-ethyldicyclohexylphosphine; (S)-1-[(R)-2-(di-(3,5-dimethylphenyl)-phosphino)ferrocenyl]ethylbis(3,5-dimethylphenyl)phosphine; (S)-1- [(R)-2-(di-2-furylphosphino)ferrocenyl]ethyldi-3,5-xylyl phosphine; (S)-1[(R)-2-(dicyclohexylphosphino)ferrocenyl]ethyldicyclohexylphosphine; (S)-1-[(R)-2-(dicyclohexylphosphino)ferrocenyl]ethyldiphenylphosphine; (S)-1-[(R)-2-(dicyclohexylphosphino)ferrocenyl]ethyldi-t-butylphosphine; (S)-1-[(R)-2-(diphenylphosphino)ferrocenyl]ethyldi(3,5-dimethylphenyl)-phosphine; (S)-1-[(R)-2-(diphenylphosphino)ferrocenyl]-ethyldicyclohexylphosphine; (S)-1-[(R)-2-(diphenylphosphino)ferrocenyl]-ethyldicyclohexylphosphine; (S)-1-[(R)-2-(diphenylphosphino)ferrocenyl]-ethyldiphenylphosphine; (S)-1-[(R)-2-(diphenylphosphino)ferrocenyl]-ethyldi-t-butylphosphine; (S)-1-[(R)-2-(di-p-tolylphosphino)ferrocenyl]-ethyldicyclohexylphosphine; and (S)-1-[(R)-2-(di-t-butylphosphino)-ferrocenyl]ethyldiphenylphosphine.

76. A transition metal complex according to claim 66 comprising a ligand selected from the group consisting of [2-(bis(3,5-dimethyl-4-methoxyphenyl)phosphino)ferrocenyl]methyldicyclohexylphosphine, [2-(bis(4-trifluoromethylphenyl)phosphino)ferrocenyl]methyl-di-t-butylphosphine; [2-(di(3,5-bis-trifluoromethylphenyl)phosphino)-ferrocenyl]methyldi(3,5-dimethylphenyl)phosphine; [2-(di(3,5-bis-trifluoromethylphenyl)phosphino)ferrocenyl]-methyldicyclohexylphosphine; [2-(di(3,5-dimethylphenyl)phosphino)-ferrocenyl]methylbis(3,5-dimethylphenyl)phosphine; [2-(di-2-furyphosphino)ferrocenyl]methyldi-3,5-xylyl phosphine; [2-(dicyclohexylphosphino)ferrocenyl]methyldicyclohexylphosphine; [2-(dicyclohexylphosphino)ferrocenyl]methyldiphenylphosphine; [2-(dicyclohexylphosphino)ferrocenyl]methyldi-t-butylphosphine; [2-(diphenylphosphino)ferrocenyl]methyldi(3,5-dimethylphenyl)phosphine; [2-(diphenylphosphino)ferrocenyl]methyldicyclohexylphosphine; [2-(diphenylphosphino)ferrocenyl]methyldicyclohexylphosphine; [2-(diphenylphosphino)ferrocenyl]methyldiphenylphosphine; [2-(diphenylphosphino)ferrocenyl]methyldi-t-butylphosphine; [2-(di-p-tolylphosphino)ferrocenyl]methyldicyclohexylphosphine; [2-(di-t-butylphosphino)ferrocenyl]methyldiphenylphosphine.; [(S)-2-(bis(3,5-dimethyl-4-methoxyphenyl)phosphino)ferrocenyl]-methyldicyclohexylphosphine; [(S)-2-(bis(4-trifluoromethylphenyl)-phosphino)ferrocenyl]methyl-di-t-butylphosphine; [(S)-2-(di(3,5-bis-trifluoromethylphenyl)phosphino)ferrocenyl]methyldi-3,5-dimethylphenyl)phosphine; [(S)-2-(di(3,5-bis-trifluoromethylphenyl)-phosphino)ferrocenyl]methyldicyclohexylphosphine; [(S)-2-(di-(3,5-dimethylphenyl)phosphino)ferrocenyl]methylbis(3,5-dimethylphenyl)-phosphine; [(S)-2-(di-2-furylphosphino)ferrocenyl]methyldi-3,5-xylyl phosphine; [(S)-2-(dicyclohexylphosphino)ferrocenyl]-methyldicyclohexylphosphine; [(S)-2-(dicyclohexylphosphino)ferrocenyl]-methyldiphenylphosphine; [(S)-2-(dicyclohexylphosphino)ferrocenyl]-methyldi-t-butylphosphine; [(S)-2-(diphenylphosphino)ferrocenyl]-methyldi(3,5-dimethylphenyl)phosphine; [(S)-2-(diphenylphosphino)-ferrocenyl]methyldicyclohexylphosphine; [(S)-2-(diphenylphosphino)-ferrocenyl]methyldicyclohexylphosphine; [(S)-2-(diphenylphosphino)-ferrocenyl]methyldiphenylphosphine; [(S)-2-(diphenylphosphino)-ferrocenyl]methyldi-t-butylphosphine; [(S)-2-(di-p-tolylphosphino)-ferrocenyl]methyldicyclohexylphosphine; [(S)-2-(di-t-butylphosphino)-ferrocenyl]methyldiphenylphosphine; [(R)-2-(bis(3,5-dimethyl-4-methoxyphenyl)phosphino)ferrocenyl]methyldicyclohexylphosphine; [(R)-2-(bis(4-trifluoromethylphenyl)phosphino)ferrocenyl]methyl-di-t-butylphosphine; [(R)-2-(di(3,5-bis-trifluoromethylphenyl)phosphino)-ferrocenyl]methyldi(3,5-dimethylphenyl)phosphine; [(R)-2-(di(3,5-bis-trifluoromethylphenyl)phosphino)ferrocenyl]-methyldicyclohexylphosphine; [(R)-2-(di-(3,5-dimethylphenyl)-phosphino)ferrocenyl]methylbis(3,5-dimethylphenyl)phosphine; [(R)-2-(di-2-furylphosphino)ferrocenyl]methyldi-3,5-xylyl phosphine; [(R)-2-(dicyclohexylphosphino)ferrocenyl]methyldicyclohexylphosphine; [(R)-2-(dicyclohexylphosphino)ferrocenyl]methyldiphenylphosphine; [(R)-2-(dicyclohexylphosphino)ferrocenyl]methyldi-t-butylphosphine; [(R)-2-(diphenylphosphino)ferrocenyl]methyldi(3,5-dimethylphenyl)phosphine; [(R)-2-(diphenylphosphino)ferrocenyl]methyldicyclohexylphosphine; [(R)-2-(diphenylphosphino)ferrocenyl]methyldicyclohexylphosphine; [(R)-2-(diphenylphosphino)ferrocenyl]methyldiphenylphosphine; [(R)-2-(diphenylphosphino)ferrocenyl]methyldi-t-butylphosphine; [(R)-2-(di-p-tolylphosphino)ferrocenyl]methyldicyclohexylphosphine; and [(R)-2-(di-t-butylphosphino)ferrocenyl]methyldiphenylphosphine.

77. A transition metal complex according to claim 66 comprising a ligand selected from the group consisting of 1-[2-(dicyclohexylphosphino)-ferrocenyl]ethyldi-t-butylphosphine; 1-[2-(diphenylphosphino)ferrocenyl]-ethyldi-t-butylphosphine; (R)-1-[(S)-2-(dicyclohexylphosphino)-ferrocenyl]ethyldi-t-butylphosphine; (R)-1-[(S)-2-(diphenylphosphino)-ferrocenyl]ethyldi-t-butylphosphine; (S)-1-[(R)-2-(dicyclohexylphosphino)ferrocenyl]ethyldi-t-butylphosphine; and (S)-1-[(R)-2-(diphenylphosphino)ferrocenyl]ethyldi-t-butylphosphine.

78. A transition metal complex according to claim 66 comprising a ligand which is 1-[2-(dicyclohexylphosphino)ferrocenyl]ethyldi-t-butylphosphine.

79. A transition metal complex according to claim 66 comprising a ligand which is (R)-1-[(S)-2-(dicyclohexylphosphino)ferrocenyl]ethyldi-t-butylphosphine; or (S)-1-[(R)-2-(dicyclohexylphosphino)ferrocenyl]ethyldi-t-butylphosphine.

* * * * *

UNITED STATES PATENT AND TRADEMARK OFFICE
CERTIFICATE OF CORRECTION

| | | |
|---|---|---|
| PATENT NO. | : 8,058,477 B2 | Page 1 of 1 |
| APPLICATION NO. | : 12/282492 | |
| DATED | : November 15, 2011 | |
| INVENTOR(S) | : Hartwig and Shen | |

It is certified that error appears in the above-identified patent and that said Letters Patent is hereby corrected as shown below:

IN THE SPECIFICATIONS:

In Column 1, beginning at line 17, please add

-- STATEMENT REGARDING FEDERALLY SPONSORED RESEARCH OR DEVELOPMENT

This invention was made with government support under GM055382 awarded by National Institute of Health. The government has certain rights in the invention. --

Signed and Sealed this
Tenth Day of January, 2012

David J. Kappos
*Director of the United States Patent and Trademark Office*